United States Patent [19]
Kaye et al.

[11] Patent Number: 5,646,249
[45] Date of Patent: Jul. 8, 1997

[54] ISOLATION AND CHARACTERIZATION OF A NOVEL CHAPERONE PROTEIN

[75] Inventors: Frederic J. Kaye, Bethesda; Gregory A. Otterson, Columbia, both of Md.

[73] Assignee: The United States of America as represented by the Department of Health and Human Services, Washington, D.C.

[21] Appl. No.: 203,905

[22] Filed: Feb. 28, 1994

[51] Int. Cl.$^6$ ...................................................... C07K 9/00
[52] U.S. Cl. .......................................... 530/350; 435/195
[58] Field of Search ............................. 530/350; 435/195

[56] References Cited

U.S. PATENT DOCUMENTS

| | | |
|---|---|---|
| 5,188,964 | 2/1993 | McGuire et al. . |
| 5,348,945 | 9/1994 | Berberian et al. .................... 514/21 |

FOREIGN PATENT DOCUMENTS

| | | |
|---|---|---|
| 9302211 | 2/1993 | WIPO . |
| 9313200 | 7/1993 | WIPO . |
| 9318146 | 9/1993 | WIPO . |

OTHER PUBLICATIONS

Bork, et al. "An ATPase Domain Common to Prokaryotic Cell Cycle Proteins, Sugar Kinases, Actin, and hsp70 Heat Shock Proteins" Proc. Natl. Acad. Sci. 89: 7290–7294 (1992).
Bole, et al. "Posttranslational Association of Immunoglobulin Heavy Chain Binding Protein with Nascent Heavy Chains in Nonsecreting and Secreting Hybridomas" J. Cell Biology 102: 1558–1566 (1986).
Chappell, et al. "The ATPase Core of a Clathrin Uncoating Protein" J. of Biological Chem. 262(2): 746–751 (1987).
Chirico, et al. "70K Heat Shock Related Proteins Stimulate Protein Translocation into Microsomes" Nature 332: 805–810 (1988).
Deshaies, et al. "A Subfamily of Stress Proteins Facilitates Translocation of Secretory and Mitochondrial Precursor Polypeptides" Nature 332: 800–805 (1988).
Flynn, et al. "Peptide–Binding Specificity of the Molecular Chaperone BiP" Nature 353: 726–730 (1991).
Flynn, et al. "Peptide Binding and Release by Proteins Implicated as Catalysts of Protein Assembly" Science 245: 385–390 (1989).
Gething, et al. "Protein Folding in the Cell" Nature 355: 33–44 (1992).
Hendrick, et al. "Molecular Chaperone Function of Heat–Shock Proteins" Annu. Rev. Biochem. 62: 349–384 (1993).
Hightower, Lawrence. "Heat Shock, Stress Proteins, Chaperones, and Proteotoxicity" Cell 66: 191–197 (1991).
Hunt, et al. "Conserved Features of Eukaryotic hsp70 Genes Revealed by Comparison with the Nucleotide Sequence of Human hsp70" Proc. Natl. Acad. Sci. 82:6455–6459 (1985).
Kassenbrock, et al. "Interaction of Heavy Chain Binding Protein (BiP/GRP78) with Adenine Nucleotides" EMBO Journal 8(5): 1461–1467 (1989).

Li, et al. "Tumor Rejection Antigen gp96/grp94 is an ATPase: Implications For Protein Folding and Antigen Presentation" EMBO Journal 12(8): 3143–3151 (1993).
Munro, et al. "An Hsp70–like Protein in the ER: Identity with the 78 kd Glucose–Regulated Protein and Immunoglobulin Heavy Chain Binding Protein" Cell 46: 291–300 (1986).
Munro, et al. "A C–Terminal Signal Prevents Secretion of Luminal ER Proteins" Cell 48: 899–907 (1987).
Otterson, et al. "Alternative Splicing of the RBP1 Gene Clusters in an Internal Exon that Encodes Potential Phosphorylation Sites" Oncogene 8: 949–957 (1993).
Pelham "Speculations on the Functions of the Major Heat Shock and Glucose–Regulated Proteins" Cell 46: 959–961 (1986).
Ritossa, et al. "A New Puffing Pattern Induced by Temperature Shock and DNP in Drosophila" Experentia 18: 571–573 (1962).
Rothman, James. "Polypeptide Chain Binding Proteins: Catalysts of Protein Folding and Related Processes in Cells" Cell 59: 591–601 (1989).
Sadis, et al. "Unfolded Proteins Stimulate Molecular Chaperone Hsc70 ATPase by Accelerating ADP/ATP Exchange" Biochemistry 31: 9406–9412 (1992).
Sanger, et al. "DNA Sequencing with Chain–Terminating Inhibitors" Proc. Natl. Acad. Sci. 74(12): 5463–5467 (1977).
Smith, et al. "Single–step Purification of Polypeptide Expressed in E. coli as Fusions with Glutathione S–transferase" Gene 67: 31–40 (1988).
Sturzbecher, et al. "Mutant p53 Proteins Bind hsp 72/73 Cellular Heat Shock–Related Proteins in SV40–transformed Monkey Cells" Oncogene 1: 201–211 (1987).
Ting, et al. "Human Gene Encoding the 78,000–Dalton Glucose–Regulated Protein and Its Pseudogene: Structure, Conservation, and Regulation" DNA 7(4): 275–286 (1988).
Tissieres, et al. "Protein Synthesis in Salivary Glands of *Drosophila melanogaster*: Relation to Chromosome Puffs" J. Mo.. Biol. 84: 389–398 (1974).
Welch, et al. "Biochemical Characterization of the Mammalian Stress Proteins and Identification of Two Stress Proteins as Glucose– and $Ca^{2+}$–Ionophore–Regulated Proteins" J. Biol. Chem. 258(11): 7102–7111 (1983).
Yeheily, et al. "The Gene for the Rat Heat–Shock Cognate, hsc70, Can Suppress Oncogene–mediated Transformation" Cell Growth & Differentiation 3: 803–809 (1992).
Adams, M.D., et al. (1993) "3400 expressed sequence tags identify diversity of transcripts from human brain" *Nature Genetics*, 4:256–267.
Wu, B., et al. (1985) "Structure and expression of the human gene encoding major heat shock protein HSP70" *Molec. Cell. Biol.*, 5(2):330–341.

*Primary Examiner*—Robert A. Wax
*Assistant Examiner*—Kawai Lau
*Attorney, Agent, or Firm*—Knobbe, Martens, Olson & Bear

[57] ABSTRACT

This invention relates to the identification and molecular characterization of the human and rat STCH chaperone protein including the corresponding gene sequence, gene fragments and protein fragments. The invention also relates antibodies to STCH and to assays to detect the presence of STCH genes, transcripts and protein in a sample.

3 Claims, No Drawings

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 2245 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 37..1452

( x i ) SEQUENCE DESCRIPTION: SEQ ID NO:1:

```
GGTACAGTCA TCACAAGCCT GTTCGGCGGG ACTGTG ATG GCC AGA GAG ATG ACG        54
                                        Met Ala Arg Glu Met Thr
                                        1               5

ATC TTA GGA TCG GCT GTT TTG ACT CTC CTG TTG GCC GGC TAT TTG GCA       102
Ile Leu Gly Ser Ala Val Leu Thr Leu Leu Leu Ala Gly Tyr Leu Ala
            10                  15                  20

CAA CAG TAT TTA CCA TTG CCT ACT CCT AAA GTG ATT GGT ATT GAT CTT       150
Gln Gln Tyr Leu Pro Leu Pro Thr Pro Lys Val Ile Gly Ile Asp Leu
        25                  30                  35

GGC ACC ACC TAT TGT TCT GTT GGG GTG TTT TTT CCT GGC ACA GGA AAA       198
Gly Thr Thr Tyr Cys Ser Val Gly Val Phe Phe Pro Gly Thr Gly Lys
    40                  45                  50

GTA AAG GTG ATT CCA GAT GAA AAT GGG CAT ATC AGC ATA CCC AGC ATG       246
Val Lys Val Ile Pro Asp Glu Asn Gly His Ile Ser Ile Pro Ser Met
55                  60                  65                  70

GTG TCT TTT ACT GAC AAT GAT GTA TAT GTG GGA TAT GAA AGC GTA GAG       294
Val Ser Phe Thr Asp Asn Asp Val Tyr Val Gly Tyr Glu Ser Val Glu
                75                  80                  85

CTG GCA GAT TCA AAT CCT CAA AAC ACA ATA TAT GAT GCC AAA AGA TTC       342
Leu Ala Asp Ser Asn Pro Gln Asn Thr Ile Tyr Asp Ala Lys Arg Phe
```

|  |  |  |  |  |  |  |  |  |  |  |  |  |  |  |  |
|---|---|---|---|---|---|---|---|---|---|---|---|---|---|---|---|
|  |  |  | 90 |  |  |  |  | 95 |  |  |  |  | 100 |  |  |

```
ATA GGC AAG ATT TTT ACC GCA GAA GAG TTG GAG GCT GAA ATT GGC AGA       390
Ile Gly Lys Ile Phe Thr Ala Glu Glu Leu Glu Ala Glu Ile Gly Arg
        105             110                 115

TAC CCA TTT AAG GTT TTA AAC AAA AAT GGA ATG GTT GAG TTT TCT GTG       438
Tyr Pro Phe Lys Val Leu Asn Lys Asn Gly Met Val Glu Phe Ser Val
    120                 125                 130

ACA AGT AAT GAG ACC ATC ACA GTG TCC CCA GAA TAT GTT GGC TCT CGA       486
Thr Ser Asn Glu Thr Ile Thr Val Ser Pro Glu Tyr Val Gly Ser Arg
135                 140                 145                 150

CTA TTG TTG AAG TTA AAG GAA ATG GCA GAG GCA TAT CTT GGA ATG CCA       534
Leu Leu Leu Lys Leu Lys Glu Met Ala Glu Ala Tyr Leu Gly Met Pro
                155                 160                 165

GTT GCC AAT GCT GTC ATT TCT GTA CCA GCA GAA TTT GAT CTA AAA CAG       582
Val Ala Asn Ala Val Ile Ser Val Pro Ala Glu Phe Asp Leu Lys Gln
                170                 175                 180

AGA AAT TCA ACA ATT GAA GCT GCT AAC CTT GCA GGA CTG AAG ATT TTG       630
Arg Asn Ser Thr Ile Glu Ala Ala Asn Leu Ala Gly Leu Lys Ile Leu
            185                 190                 195

AGG GTA ATA AAT GAA CCC ACA GCA GCA GCT ATG GCC TAT GGT CTC CAC       678
Arg Val Ile Asn Glu Pro Thr Ala Ala Ala Met Ala Tyr Gly Leu His
        200                 205                 210

AAG GCT GAC GTC TTC CAC GTC TTG GTG ATA GAC TTG GGC GGA GGA ACT       726
Lys Ala Asp Val Phe His Val Leu Val Ile Asp Leu Gly Gly Gly Thr
215                 220                 225                 230

CTA GAT GTG TCT TTA CTG AAT AAA CAA GGA GGG ATG TTT CTA ACC CGA       774
Leu Asp Val Ser Leu Leu Asn Lys Gln Gly Gly Met Phe Leu Thr Arg
                235                 240                 245

GCA ATG TCT GGA AAC AAT AAA CTT GGA GGA CAG GAC TTC AAT CAG AGA       822
Ala Met Ser Gly Asn Asn Lys Leu Gly Gly Gln Asp Phe Asn Gln Arg
                250                 255                 260

TTG CTT CAG TAC TTA TAT AAA CAG ATC TAT CAA ACA TAT GGC TTC GTG       870
Leu Leu Gln Tyr Leu Tyr Lys Gln Ile Tyr Gln Thr Tyr Gly Phe Val
            265                 270                 275

CCC TCT AGG AAA GAG GAA ATC CAC AGA TTG AGA CAA GCT GTG GAA ATG       918
Pro Ser Arg Lys Glu Glu Ile His Arg Leu Arg Gln Ala Val Glu Met
        280                 285                 290

GTC AAA TTA AAT CTG ACT CTT CAT CAA TCT GCT CAG TTG TCA GTA TTA       966
Val Lys Leu Asn Leu Thr Leu His Gln Ser Ala Gln Leu Ser Val Leu
295                 300                 305                 310

CTA ACG GTG GAG GAG CAG GAC AGG AAG GAA CCT CAC AGT AGT GAC ACT      1014
Leu Thr Val Glu Glu Gln Asp Arg Lys Glu Pro His Ser Ser Asp Thr
                315                 320                 325

GAA CTG CCA AAA GAC AAA CTT TCC TCA GCA GAT GAC CAT CGC GTG AAC      1062
Glu Leu Pro Lys Asp Lys Leu Ser Ser Ala Asp Asp His Arg Val Asn
                330                 335                 340

AGT GGG TTT GGA CGT GGC CTT TCT GAT AAG AAA AGT GGA GAA AGT CAG      1110
Ser Gly Phe Gly Arg Gly Leu Ser Asp Lys Lys Ser Gly Glu Ser Gln
            345                 350                 355

GTT TTA TTT GAA ACA GAA ATA TCA CGG AAA CTC TTT GAT ACC CTT AAT      1158
Val Leu Phe Glu Thr Glu Ile Ser Arg Lys Leu Phe Asp Thr Leu Asn
        360                 365                 370

GAA GAC CTC TTT CAG AAA ATA CTG GTA CCC ATT CAG CAA GTA TTG AAA      1206
Glu Asp Leu Phe Gln Lys Ile Leu Val Pro Ile Gln Gln Val Leu Lys
375                 380                 385                 390

GAA GGC CAC CTG GAA AAG ACT GAG ATT GAT GAG GTG GTT TTA GTT GGG      1254
Glu Gly His Leu Glu Lys Thr Glu Ile Asp Glu Val Val Leu Val Gly
                395                 400                 405

GGC TCC ACT CGT ATT CCT CGG ATC CGT CAA GTC ATT CAA GAG TTC TTT      1302
Gly Ser Thr Arg Ile Pro Arg Ile Arg Gln Val Ile Gln Glu Phe Phe
```

```
               410                          415                          420
GGA  AAA  GAT  CCC  AAC  ACA  TCT  GTA  GAC  CCT  GAC  CTA  GCA  GTA  GTA  ACG     1350
Gly  Lys  Asp  Pro  Asn  Thr  Ser  Val  Asp  Pro  Asp  Leu  Ala  Val  Val  Thr
          425                      430                     435

GGA  GTG  GCT  ATC  CAA  GCA  GGG  ATT  GAT  GGA  GGC  TCT  TGG  CCT  CTC  CAA     1398
Gly  Val  Ala  Ile  Gln  Ala  Gly  Ile  Asp  Gly  Gly  Ser  Trp  Pro  Leu  Gln
440                      445                     450

GTC  AGT  GCT  TTA  GAA  ATT  CCC  AAT  AAG  CAT  TTA  CAA  AAA  ACC  AAC  TTC     1446
Val  Ser  Ala  Leu  Glu  Ile  Pro  Asn  Lys  His  Leu  Gln  Lys  Thr  Asn  Phe
455                      460                     465                      470

AAC  TGAATTCTGC AGAAATAATG GTTATTGTG  AACTTGTCTG ATGATCTCTT                         1499
Asn
```

CCCATTTATC AGATTACCTT TTCCACAAAA GAAAGTCTCT AAAATATCAC AGAATTACCT    1559

AGAGGGCAAC ATTTAGATAC AGGAAAATTT TACATAGTGT TTTGTCTTAG GATTAGACCT    1619

GACCAGATTG ATCCTGTTTG ATTTGGAGA GATCCTATTC TAACAAATAC TCTAAAATGA     1679

TAAAATTGAG GTACAACTCT CTTAAAAGAG TATGGATAAC TATATTTTCT GGATTCTGGA    1739

GGTTGATAAC CATATGCACT AACATATAT TCTATAAACA TTAAGTAGTG CCAGTTATGA     1799

GATTCCCAGT TCTTACTAAA TTGTATTAGC AGGAGCTGGT AATTACTTGT ATTATCACAT    1859

GTAACTAATA ATTTGAACTA TACTTGAAGG ACCGTGTTGA TGTCAGGTAT TTACAGTGGT    1919

TGGAAGATAG CAGTATTATT AGATAAGCTG CATACGTAAT ATTCAGTAAC TGCCATATTA    1979

TATAACAAAT TTACATTCAC AAATTCAGTA TCCTGTTAAG TGTCATATTC TTGTAATCTG    2039

CATTCTCCAG GAGTTTTATG TGTTTAATAG ATGAATTTAT TTATTTCTA AAGGTATTCA     2099

AATGTTTCAG CACCATATAA TAGAAATACC CAATTATATT CTAGTTCCTT TATGTCCTGT    2159

ACATCATTCT CTGCTTGGAT TTCCATTATT CTGTTTGGTT AGAGAATAAA ATTGGTAATT    2219

GCATTTGAAA AAAAAAAAAA AAAAAA                                        2245

( 2 ) INFORMATION FOR SEQ ID NO:2:

( i ) SEQUENCE CHARACTERISTICS:
        ( A ) LENGTH: 471 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ala  Arg  Glu  Met  Thr  Ile  Leu  Gly  Ser  Ala  Val  Leu  Thr  Leu  Leu
1                  5                        10                       15

Leu  Ala  Gly  Tyr  Leu  Ala  Gln  Gln  Tyr  Leu  Pro  Leu  Pro  Thr  Pro  Lys
               20                      25                      30

Val  Ile  Gly  Ile  Asp  Leu  Gly  Thr  Thr  Tyr  Cys  Ser  Val  Gly  Val  Phe
          35                      40                      45

Phe  Pro  Gly  Thr  Gly  Lys  Val  Lys  Val  Ile  Pro  Asp  Glu  Asn  Gly  His
     50                      55                      60

Ile  Ser  Ile  Pro  Ser  Met  Val  Ser  Phe  Thr  Asp  Asn  Asp  Val  Tyr  Val
65                      70                      75                       80

Gly  Tyr  Glu  Ser  Val  Glu  Leu  Ala  Asp  Ser  Asn  Pro  Gln  Asn  Thr  Ile
                    85                      90                      95

Tyr  Asp  Ala  Lys  Arg  Phe  Ile  Gly  Lys  Ile  Phe  Thr  Ala  Glu  Glu  Leu
               100                     105                     110

Glu  Ala  Glu  Ile  Gly  Arg  Tyr  Pro  Phe  Lys  Val  Leu  Asn  Lys  Asn  Gly
          115                     120                     125

Met  Val  Glu  Phe  Ser  Val  Thr  Ser  Asn  Glu  Thr  Ile  Thr  Val  Ser  Pro
```

|   |   |   |   |   | 130 |   |   |   |   | 135 |   |   |   |   | 140 |   |   |   |   |
|---|---|---|---|---|---|---|---|---|---|---|---|---|---|---|---|---|---|---|---|

Glu Tyr Val Gly Ser Arg Leu Leu Leu Lys Leu Lys Glu Met Ala Glu
145                 150             155             160

Ala Tyr Leu Gly Met Pro Val Ala Asn Ala Val Ile Ser Val Pro Ala
                165             170             175

Glu Phe Asp Leu Lys Gln Arg Asn Ser Thr Ile Glu Ala Ala Asn Leu
            180             185             190

Ala Gly Leu Lys Ile Leu Arg Val Ile Asn Glu Pro Thr Ala Ala
        195             200             205

Met Ala Tyr Gly Leu His Lys Ala Asp Val Phe His Val Leu Val Ile
    210             215             220

Asp Leu Gly Gly Gly Thr Leu Asp Val Ser Leu Asn Lys Gln Gly
225             230             235             240

Gly Met Phe Leu Thr Arg Ala Met Ser Gly Asn Asn Lys Leu Gly Gly
                245             250             255

Gln Asp Phe Asn Gln Arg Leu Leu Gln Tyr Leu Tyr Lys Gln Ile Tyr
            260             265             270

Gln Thr Tyr Gly Phe Val Pro Ser Arg Lys Glu Glu Ile His Arg Leu
        275             280             285

Arg Gln Ala Val Glu Met Val Lys Leu Asn Leu Thr Leu His Gln Ser
    290             295             300

Ala Gln Leu Ser Val Leu Leu Thr Val Glu Glu Gln Asp Arg Lys Glu
305             310             315             320

Pro His Ser Ser Asp Thr Glu Leu Pro Lys Asp Lys Leu Ser Ser Ala
                325             330             335

Asp Asp His Arg Val Asn Ser Gly Phe Gly Arg Gly Leu Ser Asp Lys
            340             345             350

Lys Ser Gly Glu Ser Gln Val Leu Phe Glu Thr Glu Ile Ser Arg Lys
        355             360             365

Leu Phe Asp Thr Leu Asn Glu Asp Leu Phe Gln Lys Ile Leu Val Pro
    370             375             380

Ile Gln Gln Val Leu Lys Glu Gly His Leu Glu Lys Thr Glu Ile Asp
385             390             395             400

Glu Val Val Leu Val Gly Gly Ser Thr Arg Ile Pro Arg Ile Arg Gln
                405             410             415

Val Ile Gln Glu Phe Phe Gly Lys Asp Pro Asn Thr Ser Val Asp Pro
            420             425             430

Asp Leu Ala Val Val Thr Gly Val Ala Ile Gln Ala Gly Ile Asp Gly
        435             440             445

Gly Ser Trp Pro Leu Gln Val Ser Ala Leu Glu Ile Pro Asn Lys His
    450             455             460

Leu Gln Lys Thr Asn Phe Asn
465             470

(2) INFORMATION FOR SEQ ID NO:3:

(i) SEQUENCE CHARACTERISTICS:
        (A) LENGTH: 792 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO ( x i ) SEQUENCE DESCRIPTION: SEQ ID NO:3:

```
GAAGAGTTGG AGGCTGAAAT TGGCAGATAC CCATTTAAGG TTTTAAACAA AAATGGAATG      60
GTTGAGTTTT CTGTGACAAG TAATGAGACC ATCACAGTGT CCCCAGAATA TGTTGGCTCT     120
CGACTATTGT TGAAGTTAAA GGAAATGGCA GAGGCATATC TTGGAATGCC AGTTGCCAAT     180
GCTGTCATTT CTGTACCAGC AGAATTTGAT CTAAAACAGA GAAATTCAAC AATTGAAGCT     240
GCTAACCTTG CAGGACTGAA GATTTTGAGG GTAATAAATG AACCCACAGC AGCAGCTATG     300
GCCTATGGTC TCCACAAGGC TGACGTCTTC CACGTCTTGG TGATAGACTT GGGCGGAGGA     360
ACTCTAGATG TGTCTTTACT GAATAAACAA GGAGGGATGT TCTAACCCG AGCAATGTCT      420
GGAAACAATA AACTTGGAGG ACAGGACTTC AATCAGAGAT TGCTTCAGTA CTTATATAAA     480
CAGATCTATC AAACATATGG CTTCGTGCCC TCTAGGAAAG AGGAAATCCA CAGATTGAGA     540
CAAGCTGTGG AAATGGTCAA ATTAAATCTG ACTCTTCATC AATCTGCTCA GTTGTCAGTA     600
TTACTAACGG TGGAGGAGCA GGACAGGAAG GAACCTCACA GTAGTGACAC TGAACTGCCA     660
AAAGACAAAC TTTCCTCAGC AGATGACCAT CGCGTGAACA GTGGGTTTGG ACGTGGCCTT     720
TCTGATAAGA AAAGTGGAGA AAGTCAGGTT TTATTTGAAA CAGAAATATC ACGGAAACTC     780
TTTGATACCC TT                                                        792
```

( 2 ) INFORMATION FOR SEQ ID NO:4:

( i ) SEQUENCE CHARACTERISTICS:
    ( A ) LENGTH: 931 base pairs
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

```
GAGATCTCGT CCATGGTGCT GACCAAGATG AAGGAGATCG CCGAGGCGTA CCTGGGCTAC      60
CCGGTGACCA ACGCGGTGAT CACCGTGCCG GCCTACTTCA ACGACTCGCA GCGCCAGGCC     120
ACCAAGGATG CGGGTGTGAT CGCGGGGCTC AACGTGCTGC GGATCATCAA CGAGCCCACG     180
GCCGCCGCCA TCGCCTACGG CCTGGACAGA ACGGGCAAGG GGAGCGCAA CGTCCTGATC      240
TTTGACCTGG GCGGGGGCAC CTTCGACGTG TCCATCCTGA CGATCGACGA CGGCATCTTC     300
GAGGTGAAGG CCACGGCCGG GGACACCCAC CTGGGTGGGG AGGACTTTGA CAACAGGCTG     360
GTGAACCACT TCGTGGAGGA GTTCAAGAGA AAACACAAGA AGGACATCAG CCAGAACAAG     420
CGAGCCGTGA GGCGGCTGCG CACCGCCTGC GAGAGGGCCA GAGGACCCT GTCGTCCAGC      480
ACCCAGGCCA GCCTGGAGAT CGACTCCCTG TTTGAGGGCA TCGACTTCTA CACGTCCATC     540
ACCAGGGCGA GGTTCGAGGA GCTGTGCTCC GACCTGTTCC GAAGCACCCT GGAGCCCGTG     600
GAGAAGGCTC TGCGCGACGC CAAGCTGGAC AAGGCCCAGA TTCACGACCT GGTCCTGGTC     660
GGGGGCTCCA CCCGCATCCC CAAGGTGCAG AAGCTGCTGC AGGACTTCTT CAACGGGCGC     720
GACCTGAACA AGAGCATCAA CCCCGACGAG GCTGTGGGCT ACGGGGCGGC GGTGCAGGCG     780
GCCATCCTGA TGGGGGACAA GTCCGAGAAC GTGCAGGACC TGCTGCTGCT GGACGTGGCT     840
CCCCTGTCGC TGGGGCTGGA GACGGCCGGA GGCGTGATGA CTGCCCTGAT CAAGCGCAAC     900
TCCACCATCC CCACCAAGCA GACGCAGATC T                                   931
```

( 2 ) INFORMATION FOR SEQ ID NO:5:

( i ) SEQUENCE CHARACTERISTICS:
        ( A ) LENGTH: 357 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

```
CTTAGGATCG  GCTGTTTTGA  CTCTCCTGTT  GGCCGGCTAT  TTGGCACAAC  AGTATTTACC      60
ATTGCCTACT  CCTAAAGTGA  TTGGTATTGA  TCTTGGCACC  ACCTATTGTT  CTGTTGGGGT     120
GTTTTTTCCT  GGCACAGGAA  AAGTAAAGGT  GATTCCAGAT  GAAAATGGGC  ATATCAGCAT     180
ACCCAGCATG  GTGTCTTTTA  CTGACAATGA  TGTATATGTG  GGATATGAAA  GCGTAGAGCT     240
GGCAGATTCA  AATCCTCAAA  ACACAATATA  TGATGCCAAA  AGATTCATAG  CAAGATTTT     300
TACCGCAGAA  GAGTTGGAGG  CTGAAATTGG  CAGATACCCA  TTTAAGGTTT  TAAACAA       357
```

( 2 ) INFORMATION FOR SEQ ID NO:6:

( i ) SEQUENCE CHARACTERISTICS:
        ( A ) LENGTH: 492 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

```
AGTCTCTAAA  ATATCACAGA  ATTACCTAGA  GGGCAACATT  TAGATACAGG  AAAATTTTAC      60
ATAGTGTTTT  GTCTTAGGAT  TAGACCTGAC  CAGATTGATC  CTGTTTGATT  TTGGAGAGAT     120
CCTATTCTAA  CAAATACTCT  AAAATGATAA  AATTGAGGTA  CAACTCTCTT  AAAAGAGTAT     180
GGATAACTAT  ATTTTCTGGA  TTCTGGAGGT  TGATAACCAT  ATGCACTTAA  CATATATTCT     240
ATAAACATTA  AGTAGTGCCA  GTTATGAGAT  TCCCAGTTCT  TACTAAATTG  TATTAGCAGG     300
AGCTGGTAAT  TACTTGTATT  ATCACATGTA  ACTAATAATT  TGAACTATAC  TTGAAGGACC     360
GTGTTGATGT  CAGGTATTTA  CAGTGGTTGG  AAGATAGCAG  TATTATTAGA  TAAGCTGCAT     420
ACGTAATATT  CAGTAACTGC  CATATTATAT  AACAAATTTA  CATTCACAAA  TTCAGTATCC     480
TGTTAAGTGT  CA                                                             492
```

( 2 ) INFORMATION FOR SEQ ID NO:7:

( i ) SEQUENCE CHARACTERISTICS:
        ( A ) LENGTH: 52 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Lys  Ile  Phe  Thr  Ala  Glu  Glu  Leu  Glu  Ala  Glu  Ile  Gly  Arg  Tyr  Pro
  1              5                        10                       15
Phe  Lys  Val  Leu  Asn  Lys  Asn  Gly  Met  Val  Glu  Phe  Ser  Val  Thr  Ser
              20                        25                       30
```

```
Asn Glu Thr Ile Thr Val Ser Pro Glu Tyr Val Gly Ser Arg Leu Leu
         35                  40                  45

Leu Lys Leu Lys
     50
```

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

```
GGATCCGGCA  AGATTTTTAC  CGCAGAAGAG                                    30
```

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

```
GGATCCTTAC  TTTAACTTCA  ACAATAGTCG  AGA                               33
```

( 2 ) INFORMATION FOR SEQ ID NO:10:

( i ) SEQUENCE CHARACTERISTICS:
        ( A ) LENGTH: 135 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:10:

```
Gln Arg Leu Leu Gln Tyr Leu Tyr Lys Gln Ile Tyr Gln Thr Tyr Gly
 1               5                  10                  15

Phe Val Pro Ser Arg Lys Glu Glu Ile His Arg Leu Arg Gln Ala Val
             20                  25                  30

Glu Met Val Lys Leu Asn Leu Thr Leu His Gln Ser Ala Gln Leu Ser
         35                  40                  45

Val Leu Leu Thr Val Glu Glu Gln Asp Arg Lys Glu Pro His Ser Ser
     50                  55                  60

Asp Thr Glu Leu Pro Lys Asp Lys Leu Ser Ser Ala Asp Asp His Arg
 65                  70                  75                  80

Val Asn Ser Gly Phe Gly Arg Gly Leu Ser Asp Lys Lys Ser Gly Glu
                 85                  90                  95

Ser Gln Val Leu Phe Glu Thr Glu Ile Ser Arg Lys Leu Phe Asp Thr
```

|       |       |       | 100   |       |       |       |       | 105   |       |       |       |       | 110   |       |       |
|-------|-------|-------|-------|-------|-------|-------|-------|-------|-------|-------|-------|-------|-------|-------|-------|

Leu Asn Glu Asp Leu Phe Gln Lys Ile Leu Val Pro Ile Gln Gln Val
        115                 120                 125

Leu Lys Glu Gly His Leu Glu
    130             135

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

GGATCCAGAT TGCTTCAGTA CTTATATAAA CAG                        33

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

GGATCCTTAG TGGCCTTCTT TCAATACTTG CTG                        33

(2) INFORMATION FOR SEQ ID NO:13:

(i) SEQUENCE CHARACTERISTICS:
        (A) LENGTH: 1731 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..1730

(xi) SEQUENCE DESCRIPTION: SEQ ID NO:13:

CTG ATG GCC GGA GAG ATG ACG ATC TTA GGT TCC GCT GTC TTG ACT CTC    48
Leu Met Ala Gly Glu Met Thr Ile Leu Gly Ser Ala Val Leu Thr Leu
1               5                   10                  15

CTG TTG GCT GGC TAC TTG GCA CAA CAG TAT TTA CCA CTG CCA ACT CCA    96
Leu Leu Ala Gly Tyr Leu Ala Gln Gln Tyr Leu Pro Leu Pro Thr Pro
                20                  25                  30

AAA GTG ATT GGC ATT GAC CTG GGC ACC ACC TAC TGT TCC GTC GGT GTA   144
Lys Val Ile Gly Ile Asp Leu Gly Thr Thr Tyr Cys Ser Val Gly Val
            35                  40                  45

TTT TTT CCT GGA ACA GGG AAA GTA AAG GTG ATC CCA GAT GAA AAC GGG   192

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Phe | Phe | Pro | Gly | Thr | Gly | Lys | Val | Lys | Val | Ile | Pro | Asp | Glu | Asn | Gly |      |
|     | 50  |     |     |     |     | 55  |     |     |     |     | 60  |     |     |     |     |      |
| CAT | ATT | AGC | ATC | CCC | AGC | ATG | GTG | TCC | TTC | ACT | GAT | GGC | GAT | GTG | TAT | 240  |
| His | Ile | Ser | Ile | Pro | Ser | Met | Val | Ser | Phe | Thr | Asp | Gly | Asp | Val | Tyr |      |
| 65  |     |     |     |     | 70  |     |     |     |     | 75  |     |     |     |     | 80  |      |
| GTG | GGC | TAT | GAA | AGC | CTA | GAG | CTG | GCA | GAC | TCC | AAT | CCT | CAG | AAC | ACA | 288  |
| Val | Gly | Tyr | Glu | Ser | Leu | Glu | Leu | Ala | Asp | Ser | Asn | Pro | Gln | Asn | Thr |      |
|     |     |     |     | 85  |     |     |     |     | 90  |     |     |     |     | 95  |     |      |
| ATA | TAT | GAT | GCT | AAA | AGG | TTC | ATA | GGT | AAG | ATT | TTC | ACC | CCT | GAA | GAG | 336  |
| Ile | Tyr | Asp | Ala | Lys | Arg | Phe | Ile | Gly | Lys | Ile | Phe | Thr | Pro | Glu | Glu |      |
|     |     |     | 100 |     |     |     |     | 105 |     |     |     |     | 110 |     |     |      |
| CTG | GAG | GCT | GAA | ATT | GGC | AGA | TAC | CCA | TTT | AAG | GTT | TTA | CAC | AAA | AAT | 384  |
| Leu | Glu | Ala | Glu | Ile | Gly | Arg | Tyr | Pro | Phe | Lys | Val | Leu | His | Lys | Asn |      |
|     |     |     | 115 |     |     |     |     | 120 |     |     |     |     | 125 |     |     |      |
| GGA | ATG | GCT | GAG | TTT | TCT | GTG | ACA | AGT | AAC | GAA | ACC | ATC | ATT | GTT | TCT | 432  |
| Gly | Met | Ala | Glu | Phe | Ser | Val | Thr | Ser | Asn | Glu | Thr | Ile | Ile | Val | Ser |      |
|     | 130 |     |     |     |     | 135 |     |     |     |     | 140 |     |     |     |     |      |
| CCG | GAG | TAC | GTC | GGC | TCT | CGA | TTG | TTG | CTG | AAG | CTA | AAG | GAA | ATG | GCA | 480  |
| Pro | Glu | Tyr | Val | Gly | Ser | Arg | Leu | Leu | Leu | Lys | Leu | Lys | Glu | Met | Ala |      |
| 145 |     |     |     |     | 150 |     |     |     |     | 155 |     |     |     |     | 160 |      |
| GAG | AAA | TAC | CTT | GGA | ATG | CCG | GTT | GCC | AAT | GCT | GTC | ATT | TCT | GTG | CCA | 528  |
| Glu | Lys | Tyr | Leu | Gly | Met | Pro | Val | Ala | Asn | Ala | Val | Ile | Ser | Val | Pro |      |
|     |     |     |     | 165 |     |     |     |     | 170 |     |     |     |     | 175 |     |      |
| GCA | GAA | TTT | GAC | CTA | CAA | CAG | AGA | AAT | TCA | ACA | ATC | CAA | GCT | GCC | AAC | 576  |
| Ala | Glu | Phe | Asp | Leu | Gln | Gln | Arg | Asn | Ser | Thr | Ile | Gln | Ala | Ala | Asn |      |
|     |     |     | 180 |     |     |     |     | 185 |     |     |     |     | 190 |     |     |      |
| CTT | GCT | GGA | CTG | AAG | ATC | TTG | AGG | GTA | ATA | AAT | GAA | CCG | ACA | GCA | GCA | 624  |
| Leu | Ala | Gly | Leu | Lys | Ile | Leu | Arg | Val | Ile | Asn | Glu | Pro | Thr | Ala | Ala |      |
|     |     | 195 |     |     |     |     | 200 |     |     |     |     | 205 |     |     |     |      |
| GCG | ATG | GCC | TAT | GGT | CTC | CAC | AAG | GTT | GAT | GTC | TTC | TAC | GTG | TTA | GTC | 672  |
| Ala | Met | Ala | Tyr | Gly | Leu | His | Lys | Val | Asp | Val | Phe | Tyr | Val | Leu | Val |      |
|     | 210 |     |     |     |     | 215 |     |     |     |     | 220 |     |     |     |     |      |
| ATA | GAC | CTG | GGT | GGA | GGA | ACT | CTT | GAT | GTG | TCA | TTA | CTG | AAT | AAA | CAA | 720  |
| Ile | Asp | Leu | Gly | Gly | Gly | Thr | Leu | Asp | Val | Ser | Leu | Leu | Asn | Lys | Gln |      |
| 225 |     |     |     |     | 230 |     |     |     |     | 235 |     |     |     |     | 240 |      |
| GGA | GGA | ATG | TTT | CTA | ACA | CGC | GCA | ATG | TCT | GGA | AAC | AAC | AAA | CTT | GGA | 768  |
| Gly | Gly | Met | Phe | Leu | Thr | Arg | Ala | Met | Ser | Gly | Asn | Asn | Lys | Leu | Gly |      |
|     |     |     |     | 245 |     |     |     |     | 250 |     |     |     |     | 255 |     |      |
| GGA | CAA | GAC | TTC | AAT | CAA | AGG | CTG | CTT | CAG | TAT | TTG | TAT | AAA | GAG | ATC | 816  |
| Gly | Gln | Asp | Phe | Asn | Gln | Arg | Leu | Leu | Gln | Tyr | Leu | Tyr | Lys | Glu | Ile |      |
|     |     |     | 260 |     |     |     |     | 265 |     |     |     |     | 270 |     |     |      |
| TAT | CAA | ACA | TAC | GGC | TTT | CTC | CCT | TCT | AGG | AAA | GAG | GAG | ATC | CAC | AGA | 864  |
| Tyr | Gln | Thr | Tyr | Gly | Phe | Leu | Pro | Ser | Arg | Lys | Glu | Glu | Ile | His | Arg |      |
|     |     | 275 |     |     |     |     | 280 |     |     |     |     | 285 |     |     |     |      |
| TTA | AGA | CAA | GCA | GTG | GAA | ATG | GTC | AAG | CTA | AAC | CTG | ACG | CTT | CAT | CAG | 912  |
| Leu | Arg | Gln | Ala | Val | Glu | Met | Val | Lys | Leu | Asn | Leu | Thr | Leu | His | Gln |      |
|     | 290 |     |     |     |     | 295 |     |     |     |     | 300 |     |     |     |     |      |
| TCT | GCC | CAG | GTA | TCA | GTA | TTA | CTC | ACT | GTA | GAG | GAA | AAC | GAC | AGC | CAG | 960  |
| Ser | Ala | Gln | Val | Ser | Val | Leu | Leu | Thr | Val | Glu | Glu | Asn | Asp | Ser | Gln |      |
| 305 |     |     |     |     | 310 |     |     |     |     | 315 |     |     |     |     | 320 |      |
| AAA | CCT | CAG | AAT | GCT | GAC | TCT | AAA | CTT | CCA | GAA | GAC | CAG | CTT | ACC | CCA | 1008 |
| Lys | Pro | Gln | Asn | Ala | Asp | Ser | Lys | Leu | Pro | Glu | Asp | Gln | Leu | Thr | Pro |      |
|     |     |     |     | 325 |     |     |     |     | 330 |     |     |     |     | 335 |     |      |
| GGG | GAT | GGT | CAC | CAT | GTG | AAC | AGG | GTG | TTT | AGA | CCT | GGC | CTT | TCT | GAC | 1056 |
| Gly | Asp | Gly | His | His | Val | Asn | Arg | Val | Phe | Arg | Pro | Gly | Leu | Ser | Asp |      |
|     |     |     | 340 |     |     |     |     | 345 |     |     |     |     | 350 |     |     |      |
| AGC | ACG | AGT | GCA | AAA | AGT | CAG | GTT | TTG | TTT | GAG | ACA | GAA | GTA | TCA | CGC | 1104 |
| Ser | Thr | Ser | Ala | Lys | Ser | Gln | Val | Leu | Phe | Glu | Thr | Glu | Val | Ser | Arg |      |
|     |     | 355 |     |     |     |     | 360 |     |     |     |     | 365 |     |     |     |      |
| AAG | CTC | TTC | AAC | ACC | CTC | AAT | GAA | GAT | CTC | TTT | CAG | AAA | ATA | CTC | GTA | 1152 |

```
Lys Leu Phe Asn Thr Leu Asn Glu Asp Leu Phe Gln Lys Ile Leu Val
    370             375             380

CCC ATT CAG CAA GTA TTA AAA GAA GGC CTC TTA GAC AAG ACT GAA ATT    1200
Pro Ile Gln Gln Val Leu Lys Glu Gly Leu Leu Asp Lys Thr Glu Ile
385             390             395             400

GAT GAG GTG GTT CTA GTT GGG GGT TCT ACG CGC ATT CCT CGG ATC CGC    1248
Asp Glu Val Val Leu Val Gly Gly Ser Thr Arg Ile Pro Arg Ile Arg
            405             410             415

CAA GTT ATT CAG GAG TTC TTT GGA AAG GAC CCG AAC ACG TCT GTA GAC    1296
Gln Val Ile Gln Glu Phe Phe Gly Lys Asp Pro Asn Thr Ser Val Asp
            420             425             430

CCT GAC CTG GCA GTG GTG ACG GGA GTG GCC ATC CAA GCT GGG ATT GAT    1344
Pro Asp Leu Ala Val Val Thr Gly Val Ala Ile Gln Ala Gly Ile Asp
            435             440             445

GGA GGG TGC TGG CCT CTC CAA GTT AGT GCT TTA GAA ATT CCC AAT AAG    1392
Gly Gly Cys Trp Pro Leu Gln Val Ser Ala Leu Glu Ile Pro Asn Lys
450             455             460

CAT TTA CAG AAA ACC AAC TTC AAC TGA ACT CTG AGG GAG TGC TGG TAA    1440
His Leu Gln Lys Thr Asn Phe Asn  *  Thr Leu Arg Glu Cys Trp  *
465             470             475             480

CTG ATT GTG TCT AGT GGT GTT AAT GAT TTC CAT GTG AAC CTC CTC CAG    1488
Leu Ile Val Ser Ser Gly Val Asn Asp Phe His Val Asn Leu Leu Gln
            485             490             495

AAA TGA AGG CCA TGA AGT CAC TCA TGG ATT CAT GAG AGG ACA TTT ATA    1536
Lys  *  Arg Pro  *  Ser His Ser Trp Ile His Glu Arg Thr Phe Ile
            500             505             510

CAT GAC AAC TTT ACA TAG TAT TTT GTT TTA GAA TTG AAT ATG ACC AGA    1584
His Asp Asn Phe Thr  *  Tyr Phe Val Leu Glu Leu Asn Met Thr Arg
            515             520             525

TGA GTC TTG ATT GTG TTT GTA AAA AAG GAA AAA AAA AAA AAG AAG        1632
 *  Val Leu Ile Val Phe Val Lys Lys Glu Lys Lys Lys Lys Lys
            530             535             540

CTC AGT ATT TCT AAA GTA ACA TTG GGG GGT AAA ACT CCT GGA TTC TGG    1680
Leu Ser Ile Ser Lys Val Thr Leu Gly Gly Lys Thr Pro Gly Phe Trp
545             550             555             560

AAG TAG GTA GCC ATT TGT ACT TAC TAG TCT GGA CCT TAA TAG TGT CAA CT 1730
Lys  *  Val Ala Ile Cys Thr Tyr  *  Ser Gly Pro  *   *  Cys Gln
            565             570             575

A                                                                   1731
```

(2) INFORMATION FOR SEQ ID NO:14:

(i) SEQUENCE CHARACTERISTICS:
        (A) LENGTH: 472 amino acids
        (B) TYPE: amino acid
        (D) TOPOLOGY: linear (ii) MOLECULE TYPE: protein (iii) SEQUENCE DESCRIPTION: SEQ ID NO:14:

```
Leu Met Ala Gly Glu Met Thr Ile Leu Gly Ser Ala Val Leu Thr Leu
1               5               10              15

Leu Leu Ala Gly Tyr Leu Ala Gln Gln Tyr Leu Pro Leu Pro Thr Pro
                20              25              30

Lys Val Ile Gly Ile Asp Leu Gly Thr Thr Tyr Cys Ser Val Gly Val
            35              40              45

Phe Phe Pro Gly Thr Gly Lys Val Lys Val Ile Pro Asp Glu Asn Gly
        50              55              60

His Ile Ser Ile Pro Ser Met Val Ser Phe Thr Asp Gly Asp Val Tyr
65              70              75              80
```

-continued

| | | | | | | | | | | | | | | | |
|---|---|---|---|---|---|---|---|---|---|---|---|---|---|---|---|
| Val | Gly | Tyr | Glu | Ser 85 | Leu | Glu | Leu | Ala | Asp 90 | Ser | Asn | Pro | Gln | Asn 95 | Thr |
| Ile | Tyr | Asp | Ala 100 | Lys | Arg | Phe | Ile | Gly 105 | Lys | Ile | Phe | Thr 110 | Pro | Glu | Glu |
| Leu | Glu | Ala 115 | Glu | Ile | Gly | Arg | Tyr 120 | Pro | Phe | Lys | Val 125 | Leu | His | Lys | Asn |
| Gly | Met 130 | Ala | Glu | Phe | Ser | Val 135 | Thr | Ser | Asn | Glu | Thr 140 | Ile | Ile | Val | Ser |
| Pro 145 | Glu | Tyr | Val | Gly | Ser 150 | Arg | Leu | Leu | Leu | Lys 155 | Leu | Lys | Glu | Met | Ala 160 |
| Glu | Lys | Tyr | Leu | Gly 165 | Met | Pro | Val | Ala | Asn 170 | Ala | Val | Ile | Ser | Val 175 | Pro |
| Ala | Glu | Phe | Asp 180 | Leu | Gln | Gln | Arg | Asn 185 | Ser | Thr | Ile | Gln | Ala 190 | Ala | Asn |
| Leu | Ala | Gly 195 | Leu | Lys | Ile | Leu | Arg 200 | Val | Ile | Asn | Glu | Pro 205 | Thr | Ala | Ala |
| Ala | Met 210 | Ala | Tyr | Gly | Leu | His 215 | Lys | Val | Asp | Val | Phe 220 | Tyr | Val | Leu | Val |
| Ile 225 | Asp | Leu | Gly | Gly | Gly 230 | Thr | Leu | Asp | Val | Ser 235 | Leu | Leu | Asn | Lys | Gln 240 |
| Gly | Gly | Met | Phe | Leu 245 | Thr | Arg | Ala | Met | Ser 250 | Gly | Asn | Asn | Lys | Leu 255 | Gly |
| Gly | Gln | Asp | Phe 260 | Asn | Gln | Arg | Leu | Leu 265 | Gln | Tyr | Leu | Tyr 270 | Lys | Glu | Ile |
| Tyr | Gln | Thr 275 | Tyr | Gly | Phe | Leu | Pro 280 | Ser | Arg | Lys | Glu | Ile 285 | His | Arg |
| Leu | Arg 290 | Gln | Ala | Val | Glu | Met 295 | Val | Lys | Leu | Asn | Leu 300 | Thr | Leu | His | Gln |
| Ser 305 | Ala | Gln | Val | Ser | Val 310 | Leu | Leu | Thr | Val | Glu 315 | Glu | Asn | Asp | Ser | Gln 320 |
| Lys | Pro | Gln | Asn | Ala 325 | Asp | Ser | Lys | Leu | Pro 330 | Glu | Asp | Gln | Leu | Thr 335 | Pro |
| Gly | Asp | Gly | His 340 | His | Val | Asn | Arg | Val 345 | Phe | Arg | Pro | Gly 350 | Leu | Ser | Asp |
| Ser | Thr | Ser 355 | Ala | Lys | Ser | Gln | Val 360 | Leu | Phe | Glu | Thr | Glu 365 | Val | Ser | Arg |
| Lys | Leu 370 | Phe | Asn | Thr | Leu | Asn 375 | Glu | Asp | Leu | Phe | Gln 380 | Lys | Ile | Leu | Val |
| Pro 385 | Ile | Gln | Gln | Val | Leu 390 | Lys | Glu | Gly | Leu | Leu 395 | Asp | Lys | Thr | Glu | Ile 400 |
| Asp | Glu | Val | Val | Leu 405 | Val | Gly | Gly | Ser | Thr 410 | Arg | Ile | Pro | Arg | Ile 415 | Arg |
| Gln | Val | Ile | Gln 420 | Glu | Phe | Phe | Gly | Lys 425 | Asp | Pro | Asn | Thr | Ser 430 | Val | Asp |
| Pro | Asp | Leu | Ala 435 | Val | Val | Thr | Gly 440 | Val | Ala | Ile | Gln | Ala 445 | Gly | Ile | Asp |
| Gly | Gly 450 | Cys | Trp | Pro | Leu | Gln 455 | Val | Ser | Ala | Leu | Glu 460 | Ile | Pro | Asn | Lys |
| His 465 | Leu | Gln | Lys | Thr | Asn 470 | Phe | Asn | | | | | | | | |

( 2 ) INFORMATION FOR SEQ ID NO:15:

( i ) SEQUENCE CHARACTERISTICS:

( A ) LENGTH: 54 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

ATGGCCAGAG AGATGACGAT CTTAGGATCG GCTGTTTTGA CTCTCCTGTT GGCC      54

( 2 ) INFORMATION FOR SEQ ID NO:16:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

ATGGCCGGAG AGATGACGAT CTTAGGTTCC GCTGTCTTGA CTCTCCTGTT GGCT      54

( 2 ) INFORMATION FOR SEQ ID NO:17:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

GCTGTTTTGA CTCTCCTGTT GG      22

( 2 ) INFORMATION FOR SEQ ID NO:18:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

CTTTAACTTC AACAATAGTC GAGA      24

( 2 ) INFORMATION FOR SEQ ID NO:19:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:19:

ATTGCTTCAG TACTTATATA AACAG 25

( 2 ) INFORMATION FOR SEQ ID NO:20:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:20:

AAGGGTATCA AAGAGTTTCC GTG 23

( 2 ) INFORMATION FOR SEQ ID NO:21:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:21:

GAAATCCACA GATTGAGACA AGC 23

( 2 ) INFORMATION FOR SEQ ID NO:22:

( i ) SEQUENCE CHARACTERISTICS:
( A ) LENGTH: 438 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:22:

```
GCTGTTTTGA CTCTCCTGTT GGCCGGCTAT TTGGCACAAC AGTATTTACC ATTGCCTACT        60
CCTAAAGTGA TTGGTATTGA TCTTGGCACC ACCTATTGTT CTGTTGGGGT GTTTTTCCT       120
GGCACAGGAA AAGTAAAGGT GATTCCAGAT GAAAATGGGC ATATCAGCAT ACCCAGCATG      180
GTGTCTTTTA CTGACAATGA TGTATATGTG GGATATGAAA GCGTAGAGCT GGCAGATTCA      240
AATCCTCAAA ACACAATATA TGATGCCAAA AGATTCATAG GCAAGATTTT TACCGCAGAA      300
GAGTTGGAGG CTGAAATTGG CAGATACCCA TTTAAGGTTT TAAACAAAAA TGGAATGGTT      360
GAGTTTTCTG TGACAAGTAA TGAGACCATC ACAGTGTCCC CAGAATATGT TGGCTCTCGA      420
```

CTATTGTTGA AGTTAAAG 438

( 2 ) INFORMATION FOR SEQ ID NO:23:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:23:

GGATCCGTCA AGTCATTCAA GAG 23

( 2 ) INFORMATION FOR SEQ ID NO:24:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:24:

TATGACACTT AACAGGATAC TGA 23

( 2 ) INFORMATION FOR SEQ ID NO:25:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:25:

GAAGAGTTGG AGGCTGAAAT TGGC 24

( 2 ) INFORMATION FOR SEQ ID NO:26:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:26:

AAGGGTATCA AGAGTTTCCG TG 2289

072396

ISOLATION AND CHARACTERIZATION OF A NOVEL CHAPERONE PROTEIN

FIELD OF THE INVENTION

This invention relates to chaperone proteins and particularly to a member of the major stress70 class of chaperone proteins.

BACKGROUND OF THE INVENTION

The coordinated events underlying protein folding, translocation across membranes, post-translational modifications and multi-unit assembly are essential to the viability of all cellular organisms. Recent data have demonstrated that conserved members of the "stress" or "heat shock" protein (HSP) family participate in these processing events by their ability to bind denatured or misfolded peptide sequences and then to release these polypeptide chains by an ATP-dependent mechanism. For a review of stress and heatshock proteins see Pelham, et al. *Cell* 46: 959–961, 1986, Hightower, et al., *Cell* 66: 191–197, 1991 and Gething, et al., *Nature* 355: 33–45, 1992. Although HSP members were first identified by their accumulation following cell exposure to elevated temperatures (Ritossa, et al. *Experientia* 18: 571–573, 1962; Tissieres et al., *J. Mol. Biol.* 84: 389–398, 1974), it was later recognized that a significant subset of these proteins was constitutively expressed and that cell incubations with a variety of metabolic poisons could result in gene induction (Welch et al., *J. Biol. Chem.* 258: 7102–7111, 1983). In eukaryotes, certain HSP products have been localized to specific cellular fractions, such as the cytosol, nucleus, endoplasmic reticulum or mitochondria, and recent experimental models have implicated these "chaperones" with facilitating protein transport across these specialized compartments (Chirico, et al. *Nature* 332: 805–810, 1988 and Deshaies et al., *Nature* 332: 800–805, 1988).

The stress70 gene comprise a group of related proteins within the larger HSP family. The stress70 gene family is complex and includes members from varied stages of evolution, including bacterial (dnaK, Bardwell, et al. *Proc. Natl. Acad. Sci.* 81: 848–852, 1984), yeast (kar2, ssa1, ssa2 and ssc1, Ingolia, et al. *Mol. Cell. Biol.* 2: 1388–1398, 1982; Chirico et al., supra; Deschaies et al., supra; Normington, et al. *Cell* 57: 1223–1236, 1989; and Rose, et al. *Cell* 57: 1211–1221, 1989) and mammalian species (hsp70, hsc70, grp78/BiP and pbp74, Mues, et al. *J. Biol. Chem.* 261: 874–877, 1986; Munro, et al. *Cell* 46: 291–300, 1986; Gething, et al. supra; and Domanico, et al. *Mol. Cell. Biol.* 13: 3598–3610, 1993). Structural analyses of these gene products have shown a highly conserved amino terminal domain that encodes ATP-binding and hydrolysis activity, and a less conserved carboxyl terminal portion that is required for peptide binding (Chappell, et al. *J. Biol. Chem.* 262: 746–751, 1987; Flajnik, et al. *Immunogenetics* 33: 295–300, 1991; and Rippmann, et al. *EMBO J.* 10: 1053–1059, 1991). The recognition that an hsp70-related gene encoded an abundant endoplasmic reticulum (ER) product identical to both the mammalian immunoglobulin binding protein (BiP) and the glucose-regulated protein (GRP78) suggested a specific role for stress70 proteins in the folding and assembly of newly synthesized proteins in the ER (Munro, et al. supra). This confirmed the hypothesis that stress70 molecules participate in protein processing during normal and stressed conditions (Bole, et al. *J. Cell. Biol.* 102: 1558–1566, 1986; Gething, et al. *Cell* 46: 939–950, 1986; and Pelham, et al. supra). GRP78/BiP has since been widely studied and shown to be targeted and retained in the ER by an amino terminal signal peptide and a carboxyl terminal ER retention signal (the tetrapeptide KDEL) (Munro, et al. *Cell* 48: 899–907, 1987 and Munro, et al., 1986 supra). Functional experiments have demonstrated that GRP78/BiP can reversibly bind in vitro to short peptides with relatively hydrophobic amino acid residues that are proposed to represent exposed domains on unfolded or misfolded proteins within the ER. In addition, GRP78/BiP encodes a peptide-stimulated ATPase activity that may then drive the protein folding process toward completion (Flynn, et al. *Nature* 353: 726–730, 1991 and Flynn, et al. *Science* 245: 385–390, 1989).

We describe the cloning of a constitutively expressed member of the stress70 protein chaperone family, designated Stch. Although Stch encodes a protein (STCH) with striking amino acid identity to HSP70 and BiP, it also has significant differences from the previously reported stress70 products. These unique differences include the presence of a unique hydrophobic signal sequence, a 50 amino acid insertion within the ATP-binding domain, and the absence of a carboxyl terminal peptide-binding domain. These structural features suggest the presence of a truncated stress70 product within protein secretory pathways that resembles the N-terminal proteolytic fragments of HSC70 and BiP (Chappell et al., 1987 supra and Kassenbrock, et al. *EMBO J.* 8: 1461–1467, 1989). Using antibodies to STCH antisera, we have confirmed these predictions and demonstrated that Stch encodes a smaller product (p60) which is highly enriched within the lumen of the cellular microsome fraction. In addition, we have shown data indicating that STCH expression varies between cell types. STCH exhibits ATPase activity that, in contrast to other HSP70-like molecules, is independent of peptide stimulation.

SUMMARY OF THE INVENTION

This invention relates to a novel chaperone protein, STCH. The human and rat Stch gene sequence and protein sequence are disclosed. The human and rat STCH proteins shared greater than 90% homology. Methods are disclosed for identifying STCH protein from other species. The protein sequence was compared to similar proteins and the sequence showed a similarity to the stress70 protein family. In particular, the few regions that did have homology to human HSP70 and human BiP were those regions involved in ATP binding. The ATPase activity of STCH was confirmed and the STCH gene localized to the long arm of human chromosome 21. The Stch gene sequence and nucleic acid fragments from the sequence are useful for detecting the presence of Stch in various tissue and transcriptional levels of Stch were found to vary between different cell types. Stch probes are useful for identifying the long arm of chromosome 21 for genetic analysis. Antibodies to Stch were produced and they were useful for identifying STCH protein in a sample.

Thus, in a preferred embodiment of this invention, a recombinant or synthetic nucleic acid molecule encoding protein consisting essentially of SEQ ID NO:1 or SEQ ID NO:13, recombinant homologs thereof and recombinant or synthetic nucleic acid molecules of at least 30 consecutive nucleotides in length from SEQ ID NO:1 or SEQ ID NO:13 are disclosed. These recombinant or synthetic nucleic acid molecules preferably hybridize after denaturation to SEQ ID NO:1 or SEQ ID NO:13 under salt and temperature conditions equivalent to 2×SSC and 37° C. The nucleic acid molecules are preferably DNA, including single stranded DNA, or RNA. These molecules are prepared from either the sense or the antisense strand and in one embodiment, these sequences are derived from either a human or a rat. In a preferred embodiment of this invention, the recombinant nucleic acid molecules consist essentially of SEQ ID NO:15 or SEQ ID NO:16.

In another preferred embodiment of this invention, a gene vector is contemplated that contains a recombinant or synthetic nucleic acid molecule consisting essentially of SEQ ID NO:1 or SEQ ID NO:13, recombinant homologs thereof and recombinant or synthetic nucleic acid molecules of at least 30 consecutive nucleotides in length. Preferably this vector is capable of directing the expression of a polypeptide encoded by SEQ ID NO:1 or SEQ ID NO:13. Protein expression is contemplated from either prokaryotic or eukaryotic cells. Thus, cells containing recombinant or synthetic nucleic acid molecules consisting essentially of SEQ ID NO:1 or SEQ ID NO:13, recombinant homologs thereof and recombinant or synthetic nucleic acid molecules of at least 30 consecutive nucleotides in length are also contemplated in this invention.

Synthetic, recombinant or purified protein consisting essentially of SEQ ID NO:2 or SEQ ID NO:14 or recombinant or synthetic forms of protein homologs thereof are also disclosed in this invention. Similarly, purified recombinant or synthetic peptide consisting of at least 15 consecutive amino acids from SEQ ID NO:2 or SEQ ID NO:14 are contemplated. A substantially purified protein isolated from a cell is claimed. This protein is characterized by a molecular mobility on a sodium dodecyl sulfate polyacrylamide electrophoresis gel that is equivalent to the molecular mobility of a protein having a molecular weight of between 59 and 73 kD, a truncated carboxyl terminal peptide-binding domain, a protein-independent core ATPase, and a hydrophobic leader peptide, wherein the gene expressing this protein is induced following cell incubation with the calcium ionophore A23187 and wherein the native form of the protein localizes within the microsome lumen of a cell.

In yet another preferred embodiment of this invention, purified antibodies specifically recognizing polypeptide consisting of at least 15 consecutive amino acids from SEQ ID NO:2 and Fab and F(ab')$_2$ fragments recognizing polypeptide consisting of at least 15 consecutive amino acids from SEQ ID NO:2 are also contemplated and disclosed in this invention.

Still further, a method is disclosed for making recombinant polypeptide encoded by SEQ ID NO:1 or SEQ ID NO:13, comprising: introducing a gene vector encoding polypeptide into a host cell, wherein the polynucleotide encoding the polypeptide consists essentially of at least 60 sequential nucleotides from SEQ ID NO:1, expressing the polypeptide in the cell, isolating the polypeptide from the cell, and purifying the polypeptide from the cell. In one embodiment of this method, the polypeptide is a fusion protein.

In another preferred method of this invention, a method is provided for detecting Stch transcripts in a tissue sample, comprising: preparing a tissue sample for mRNA detection, incubating the sample with a single strand recombinant or synthetic DNA molecule comprising at least 30 consecutive nucleotides from SEQ ID NO:1, wherein the DNA molecule is capable of hybridizing to Stch under salt and temperature conditions equivalent to 2×SSC and 37° C. The method further comprises detecting hybridizing nucleic acid sequences in the sample and comparing the level of hybridization in the tissue sample with the level of hybridization in a control sample.

In another preferred method if this invention, a method is disclosed for determining the number of copies of Stch in a cell genome, comprising: preparing a cell sample for gene detection, digesting the DNA in the sample with a restriction endonuclease, electrophoretically separating the DNA in the sample, incubating the separated DNA with a single strand recombinant or synthetic DNA molecule comprising at least 30 consecutive nucleotides from SEQ ID NO:1, wherein the DNA molecule is capable of hybridizing to Stch under salt and temperature conditions equivalent to 2×SSC and 37° C., processing the sample to detect hybridization between the single strand DNA molecule and the DNA in the sample; and determining the number of Stch copies in the cell genome.

A method is also disclosed and claimed for detecting the present of STCH protein in a cell sample, comprising isolating a cell sample from a patient, processing the cell sample to permit STCH detection in the cells, incubating the sample with substantially purified antibody specifically recognizing STCH, and detecting the presence of antibody binding to STCH in the sample. In one embodiment of this method the detection step employs immunofluorescence. In other embodiments of this method, the method is an Enzyme linked immunosorbent assay, an immunoblot assay or a Western Blot assay.

The invention also discloses a method for identifying chromosome 21 in a cell sample, comprising: obtaining a cell sample, preparing chromosome spreads from the cell sample, isolating a nucleic acid sequence of at least 30 consecutive nucleotides from SEQ ID NO:1, SEQ ID NO:13, or a homolog thereof, incubating the probe with the chromosome spreads, and detecting hybridization of the probe with the chromosome spread.

DETAILED DESCRIPTION OF THE INVENTION

The gene sequence for the rat and human Stch chaperone proteins are disclosed. Methods are disclosed for isolating, purifying and sequencing other members of the Stch chaperone family of stress70 proteins. The proteins were expressed from gene vectors and antibodies specific for the protein were produced and used in immunologic assays.

The gene sequence and probes derived from the gene sequence are useful for developing diagnostic assays to detect the presence or absence of the Stch chaperone protein in a vertebrate and to assess the presence or absence of the gene sequence or transcripts thereof in a variety of tissues. The Stch gene localizes to chromosome 21q. Therefore STCH probes are useful for detecting chromosome 21 and in particular for identifying the chromosome 21q location.

In addition, the gene sequence and probes derived therefrom are useful for quantitating the amount of gene transcript in normal and transformed tissues.

Another chaperone protein, BiP, has structural similarities to STCH. BiP transcript levels have been elevated in transformed cells. Similarly transcript levels of STCH can also be altered in transformed cells. STCH antibodies are useful for detecting the presence of the protein in a cell sample. STCH protein has a protein independent ATPase activity and is useful in assays to detect the presence of ATP in a sample. The incorporation of the gene sequence into a gene vector and the expression of the protein from the vector system permit one with skill in the art to obtain purified quantities of the STCH protein. This purified protein has a number of additional applications. For example, chaperone proteins are known to facilitate protein folding in vivo and in vitro. In particular, those skilled in the art of chaperone protein activity, and in particular those knowledgeable of stress70 protein family activity recognize that stress70 proteins are polypeptide-chain binding proteins which interact with broad specificity with unfolded polypeptides (Rothman, *Cell* 59:591–601, 1989). Thus, the addition of the STCH chaperone protein in translation systems, alone or as a cocktail of chaperone proteins, is useful for the production of protein in native conformation, as an additive to promote conformational folding during dialysis following urea extractions, or the like. Further, chaperone proteins are useful for X-ray crystallographic studies to promote native protein folding prior to crystal formation.

CHARACTERIZATION OF Stch GENE

A. Molecular Cloning of a Novel Stress70 Protein Chaperone

The novel cDNA clone was initially identified in assays to study gene products that bind the retinoblastoma protein. The gene sequence was obtained from a cDNA clone derived from a K562 erythroleukemia cell line library that, on the basis of its predicted amino acid sequence, encoded a novel member of the stress70 protein chaperone family. Example I provides a preferred method for the isolation of Stch-containing clones, clones containing Stch homologs or gene sequences having sufficient complementary to Stch that the sequences bind to Stch derived gene probes in hybridization conditions equivalent to 2×SSC at 37° C. For purposes of this invention, a "homolog" is defined as a sequence sufficiently complementary to a second nucleic acid sequence such that it will hybridize to the first nucleic acid sequence in a solution of 2×SSC at 37° C. The Stch cDNA obtained from less stringent hybridization assays using the retinoblastoma binding protein-1 gene (Otterson, et al., *Oncogene* 8: 949–957, 1993 which is hereby incorporated by reference) did not exhibit significant nucleotide homology to the retinoblastoma binding protein-1 gene. While Stch was identified using the methods of Otterson, et al., Stch was not disclosed in this reference, nor was it isolated in preparation for publication of this reference. No Stch containing clones were analyzed during the initial study disclosed by Otterson, et al., supra.

In later studies, the Stch containing clone was studied and overlapping clones were obtained from the K562 library. The sequences identified by these clones corresponded to a 2.2 kilobase (kb) cDNA transcript that was initiated by a consensus AUG flanking sequence (Kozak, et al. *Nucl. Acids Res.* 12: 857–872, 1984). This cDNA encoded a single long open reading frame of 471 codons.

Nucleic acid isolated from the cDNA was subjected to di-deoxy nucleotide sequencing (Sanger, et al. *Proc. Natl. Acad. Sci. USA* 74:5463–5467, 1977, which is hereby incorporated by reference) and the human Stch sequence was verified using at least two independent PCR products. The nucleotide sequence of human Stch (SEQ ID NO:1) is provided in Table I together with the amino acid sequence of the protein (SEQ ID NO:2). Referring to Table I, four potential N-glycosylation sites (N-X-S/T) at codons 137, 184, 298 and 427 are identified in bold print. Amino acid residues are designated by their single-letter code. The sequence has a GenBank/EMBL accession number of U04735. A rat Stch sequence has also been identified. This gene sequence is provided as SEQ ID NO: 13. The corresponding protein sequence (STCH) is designated SEQ ID NO: 14. The rat sequence was identified using pStch1 (SEQ ID NO: 3) under the low stringency hybridization conditions provided in Example II. Table II provides a comparison of the amino acid sequences of human and rat STCH. The comparison indicates that the protein sequences are virtually identical. Thus, STCH appears to be well conserved among eukaryotes.

Two other methods were used to confirm the nucleotide sequence of human Stch. In a first set of experiments cDNA clones were isolated and sequenced from another human cDNA library (H69, Stratagene, La Jolla, Calif.) and in a second set of experiments the sequence was obtained using a reverse-transcription polymerase chain reaction (PCR) technique (RT-PCR) using total RNA extracted from H2172 and H2009 human carcinoma cell lines (American Type Culture Collection, Gaithersburg, Md.). Both methods are disclosed in Example I.

Thus, this invention includes recombinant nucleic acid molecules encoding protein that consist of SEQ ID NO: 1 or SEQ ID NO: 13. Example I enables those with skill in the art to use SEQ ID NO: 1 or SEQ ID NO: 13 to recreate full length recombinant molecules or fragments thereof. A fragment length of at least 30 consecutive nucleotides is preferred. Further, Example I enables those with skill in the art to identify and isolate recombinant homologs capable of hybridizing with SEQ ID NO: 1 or SEQ ID NO: 13 under salt and temperature conditions equivalent to 2×SSC and 37° C. Those skilled in the art are readily able to employ either RNA or double or single stranded DNA molecules from either the sense or antisense strands of SEQ ID NO: 1 or SEQ ID NO: 13 in a variety of molecular assays.

An analysis of the translated amino acid sequence using the BlastP protein homology search program (Altschul, et al. *J. Mol. Biol.* 215: 403–410, 1990) identified homologies between the human Stch gene sequence and the gene sequence of the stress70 protein family. These homologies were primarily clustered within five ATP-binding domains. Homologies among

TABLE I

```
GGTACAGTCATCACAAGCCTGTTCGGCGGACTGTGATGGCCAGAGAGATGACGATCTTAGGATCGGCTGTTTGACTCTCCTGTTGGCCGGCTATTTGGCCAACAGTATTTACCATTG  120
                                  M  A  R  E  M  T  I  L  G  S  A  V  L  T  L  L  L  A  G  Y  L  A  Q  Q  Y  L  P  L

CCTACTCCTAAAGTGATTGGTATTGATCTTGGCACCACCTATTGTTCTGTTGGGGTGTTTTTTCCTGGCACAGGAAAAGTAAAGGTGATTCCAGATGAAAATGGGCACACATATCAGCATATCCC  240
 P  T  P  K  V  I  G  I  D  L  G  T  T  Y  C  S  V  G  V  F  F  P  G  T  G  K  V  K  V  I  P  D  E  N  G  H  I  S  I  P

AGCATGGTCTTTTACTGACAATGATGTATATGTGGGATATGAAAGCGTAGAGCTGGCAGATTCAAATCCTCAAAACACAATATATGATGCAAAAGATTCATAGGCAAGATTTTTACC  360
 S  M  V  S  F  T  D  N  D  V  Y  V  G  Y  E  S  V  E  L  A  D  S  N  P  Q  N  T  I  Y  D  A  K  R  F  I  G  K  I  F  T

GCAGAAGAGTTGGAGGCTGAAATTGGCAGATACCCATTTAAGGTTTTTAAACAAAAATGTTGAGTTTTCTGTGACAAGTAATGAGACCATCACAGTGTCCCAGAATATGTTGGC  480
 A  E  E  L  E  A  E  I  G  R  Y  P  F  K  V  L  N  K  N  G  M  V  E  F  S  V  T  S  N  E  T  I  T  V  S  P  E  Y  V  G

TCTCGACTATTGTTGAAGTTAAAGGAAATGGCAGAGGCATATCTTGGAATGCCAATGTGTCCAGTGCCAATGCTGTCATTTCTGTACCAGCAGAATTTGATCTAAACAGAGAAATTCAACAATTGAA  600
 S  R  L  L  K  L  K  E  M  A  E  A  Y  L  G  M  P  V  A  N  A  V  I  S  V  P  A  E  F  D  L  K  Q  R  M  S  T  I  E

GCTGCTAACCTTGCAGGACTGAAGATTTTGAGGGTAATAAATGAACCCACAGCAGCAGCTATGGCTATGGTCTCCACAAGGCTGACGTCTTCCACGTCTTGGTGATAGACTTGGGCGGA  720
 A  A  N  L  A  G  L  K  I  L  R  V  I  N  E  P  T  A  A  A  M  A  Y  G  L  H  K  A  D  V  F  H  V  L  V  I  D  L  G  G

GGAACTCTAGATGTGTCTTTACTGAATAAACAGGAGGATGTTTCTAACCCGAGCAATGTCTGAAAACAATAAACTTGGAGGACAGGACTTCAATCAGAGATTGCTTCAGTACTTATATAT  840
 G  T  L  D  V  S  L  L  N  K  Q  G  G  M  F  L  T  R  A  M  S  G  N  N  K  L  G  G  Q  D  F  N  Q  R  L  L  Q  Y  L  Y

AAACAGATCTATCAAACATATGGCTTCGTGCCCTCTAGGAAAGAGGAAATCCACAGATTGAGACAAGCTGTGGAAATGGTCAAATTAAATCTGACTCTTCATCAATCTGCTCAGTTGTCA  960
 K  Q  I  Y  Q  T  Y  G  F  V  P  S  R  K  E  E  I  H  R  L  R  Q  A  V  E  M  V  K  L  N  L  T  L  H  Q  S  A  Q  L  S
```

TABLE I-continued

```
GTATTACTAACGGTGTGGAGGAGCAGGACAGGAAGGAACCTCACAGTAGTGCCAAAGACAAACTTTCCTCAGCAGATGACCTGAACGCGTGAACAGTGGGTTTGGACGTCGC    1080
         +         +         +         +         +         +         +         +         +         +
  V  L  L  T  V  E  E  Q  D  R  K  E  P  H  S  S  D  T  E  L  P  K  D  K  L  S  S  A  D  D  H  R  V  N  S  G  F  G  R  G

CTTTCTGATAAGAAAAGTGGAGAAAGTCAGGTTTTATTTGAAACAGAAATATCACGGAAACCTCTTTGATACCCTTAATGAAGACCTCTTTCAGAAAATACTGGTACCCATTCAGCAAGTA    1200
         +         +         +         +         +         +         +         +         +         +
  L  S  D  K  K  S  G  E  S  Q  V  L  F  E  T  E  I  S  R  K  L  F  D  T  L  N  E  D  L  F  Q  K  I  L  V  P  I  Q  Q  V

TTGAAAGAAGGCCACCTGGAAAGACTGAGATTGATGAGGTGGTTTTAGTTGGGGTTCCACTCGTATTCCTCGGATCCGTCAAGTCTTTTGGAAAAGATCCAACACA    1320
         +         +         +         +         +         +         +         +         +         +
  L  K  E  G  H  L  E  K  T  E  I  D  E  V  V  L  V  G  G  S  T  R  I  P  R  I  R  Q  V  I  Q  E  F  F  G  K  D  P  N  T

TCTGTAGACCCTGACCTAGCAGTAGTAACGGGAGTGGCTATCCAAGCAGGGATTGATGGAGGCTCTCCAAGTCAGTGCTTTAGAAATTCCCAATAAGCATTTACAAAAAACC    1440
         +         +         +         +         +         +         +         +         +         +
  S  V  D  P  D  L  A  V  V  T  G  V  A  I  Q  A  G  I  D  G  G  S  W  P  L  Q  V  S  A  L  E  I  P  N  K  H  L  Q  K  T

AACTTCAACTGAATTCTGCAGAAATAATGGTTATTTGTGAACTTGTCTGATGATCTCTTCCCATTATCAGATTACCTTTCCACAAAAGAAGTCTCTAAATATCACAGATTTACCTA    1560
         +         +         +         +         +         +         +         +         +         +
  N  F  N  *

GAGGGCAACATTTAGATACAGGAAAATTTTACATAGTGTTTTGTCTTAGGATTGATCCGTGTTGATTTTGGAGAGATCCTATTCTAACAAATACTCTAAAATGAT    1680
         +         +         +         +         +         +         +         +         +         +

AAAATTGAGGTACAACTCTCTTAAAAGAGTATGGATAACTATATTTTCTGATTCTGGAGGTTGATAACCATATGCACTTAACCATATAAACATTAAGTAGTGCCAGTTATGAG    1800
         +         +         +         +         +         +         +         +         +         +

ATTCCCAGTTCTTACTAAATTGTATTAGCAGGAGCTGGTAATTACTTGTATTATCACATGTAACTAATAATTGAACTATACTTGAAGGACCGTGTTGATGTCAGGTATTTACAGTGGTT    1920
         +         +         +         +         +         +         +         +         +         +

GGAAGAGATAGCAGTATTATTAGATAAGCTGCATACGTAATATTCAGTAACTGCCATATATTATAACAAATTTACATTCACAAATTCAGTATCCGTTAAGTGTCATATTCTTGTAATCTGC    2040
         +         +         +         +         +         +         +         +         +         +
```

TABLE I-continued

```
ATTCTCCAGGAGTTTATGTGTTAATAGATGAATTTATTTATTCTAAAGGTATTCAAATGTTTCAGCACCATATAATAGAAATACCCAATTATATTCAGTTCCTTTATGTCCTGTA  2160

CATCATTCTCTGCTTGGATTTCCATTATTCTGTTTGGTTAGAGAATAAAATTGGTAATTGCATTTGAAAAAAAAAAAAA  2246
```

TABLE II

COMPARISON OF HUMAN AND RAT STCH SEQUENCES human
MAREMTILGSAVLTLLLAGYLAQQYLPLPTPKVIGIDLGTTYCSVGVFFPGTGK
rat
MAGEMTILGSAVLTLLLAGYLAQQYLPLPTPKVIGIDLGTTYCSVGVFFPGTGK
human
VKVIPDENGHISIPSMVSFTDNDVYVGYESVELADSNPQNTIYDAKRFIGKIFT
rat
VKVIPDENGHISIPSMVSFTDGDVYVGYESLELADSNPQNTIYDAKRFIGKIFT
human
AEELEAEIGRYPFKVLNKNGMVEFSVTSNETITVSPEYVGSRLLLKLKEMAEAY
rat
PEELEAEIGRYPFKVLNKNGMAEFSVTSNETIIVSPEYVGSRLLLKLKEMAEKY
human
LGMPVANAVISVPAEFDLKQRNSTIEAANLAGLKILRVINEPTAAAMAYGLHKA
rat
LGMPVANAVISVPAEFDLQQRNSTIQAANLAGLKILRVINEPTAAAMAYGLHKV
human
DVFHVLVIDLGGGTLDVSLLNKQGGMFLTRAMSGNNKLGGQDFNQRLLQYLYKQ
rat
DVFYVLVIDLGGGTLDVSLLNKQGGMFLTRAMSGNNKLGGQDFNQRLLQYLYKE
human
IYQTYGFVXSRKEEIHRLRQAVEMVKLNLTLHQSAQLSVLLTVEEQDRKEPHSS
rat
IYQTYGFLPSRKEEIHRLRQAVEMVKLNLTLHQSAQVSVLLTVEENDSQKPQNA
human
DTELPKDKLSSADDHRVNSGFGRGLSDKKSGESQVLFETEISRKLFDTLNEDLF
rat
DSKLPEDQLTPGDGHHVNRVFRPGLSDSTSAKSQVLFETEVSRKLFNTLNEDLF
human
QKILVPIQQVLKEGHLEKTEIDEVVLVGGSTRIPRIRQVIQEFFGKDPNTSVDP
rat
QKILVPIQQVLKEGLLDKTEIDEVVLVGGSTRIPRIRQVIQEFFGKDPNTSVDP
human
DLAVVTGVAIQAGIDGGSWPLQVSALEIPNKHLQKTNFN*
rat
DLAVVTGVAIQAGIDGGCWPLQVSALEIPNKHLQKTNFN* stress70 protein ATP-binding domains are disclosed by Bork, et al. (*Proc. Natl. Acad. Sci.* 89: 7290–7294, 1992). The amino acid identity in these domains defines this group as distinct from other less conserved ATP-binding proteins. This gene was designated Stch (for Stress/chaperone) and its encoded protein as STCH. The amino acids of STCH were aligned with the amino acids of human HSP70 and human BiP (from Hunt, et al. *Proc. Natl. Acad. Sci.* 82: 6455–6459, 1985 and Ting, et al. *DNA* 7: 375–386, 1988 respectively). Five conserved regions involved in ATP binding (phosphate1 (18aa), connect1 (17aa), phosphate2 (21aa), adenosine (27aa) and connect2 (21aa) identified by Bork, et al., supra, were present in STCH with some modifications. Thus, with the exception of the ATP binding domains, the remaining amino acid sequence was quite different from either HSP70 or BiP.

As compared with HSP70, STCH contains a unique hydrophobic leader peptide sequence (MAREMTILGSAVLTLLLAGYLA) and has a 50 residue insertion between the phosphate2 and the adenosine ATP-binding sequence motifs (see Bork et al., supra for HSP70 information). In addition, STCH has truncated 236 and 227 carboxyl terminal residues as compared with HSP70 and BiP sequences respectively.

B. Distribution of Stch in Vertebrate Tissues

Assays were developed to test for the presence or absence of Stch between species and among different tissues. To examine whether Stch existed as a single-copy or multi-copy gene and to determine whether Stch is present in different species, DNA blot analysis was performed using an internal cDNA probe, designated pStch1 (SEQ ID NO:3 corresponding to Stch nucleotide co-ordinates #364–1155). The probe was obtained by PCR amplification using SEQ ID NO:25 and SEQ ID NO:26 followed by gel fragment purification. The probe was used under low stringency hybridization and washing conditions (see Example II). Genomic DNA from human, rat and Drosophila tissues (Clontech, Palo Alto) was digested to completion with BamHI and EcoRI restriction enzymes, and Southern blot analysis was performed under low-stringency hybridization and washing conditions (see Example II). The analysis demonstrated that Stch was present as a single locus in both human and rat cells, but was not detectable under the hybridization conditions set forth in Example II in the Drosophila genome. These experiments further indicated that Stch cDNA does not hybridize even at low stringency with other members of the stress70 gene family.

C. Stch Transcript Levels Vary Between Tissue Type

Transcription levels of Stch were assayed from human heart, brain, placenta, lung, liver, skeletal muscle, kidney and pancreas using the pStch1 probe (SEQ ID NO:3). Stch was expressed as 4.4 and 2.4 kb transcripts in all human adult tissues examined using Southern blot analysis (see Example II). The Stch transcript was present in all tissues tested. The steady-state levels of the 2.4 kb transcript varied greatly among the different adult tissues examined with expression greatest in placenta, kidney, pancreas and liver. Brain, heart, and lung expressed undetectable to trace levels of this transcript.

D. Induction of Stch with a Calcium Ionophore mRNA levels were evaluated following heat shock treatment and after exposure to the calcium ionophore A23187 to determine if Stch expression was temperature inducible, like many members of the stress70 family, or whether Stch was expressed constitutively and to determine if gene expression was altered by exposure to a calcium ionophore. A preferred heat shock strategy and methods for exposing cells to calcium ionophores to assay for their effect on gene expression are provided in Example II. RNA was isolated from treated cells and mRNA was separated on Northern gels. The RNA was transferred to nitrocellulose and hybridized with the Stch specific probe pStch1 (SEQ ID NO:3) or the HSP70 probe, pH2.3 (SEQ ID NO:4). Stch was not induced by elevated temperatures; however, Stch mRNA expression was enhanced following exposure to the calcium ionophore A23197. The stress 70 protein gene GRP78/BiP is also induced after exposure to the calcium ionophore A23197 (Munro, et al., 1986, supra) and these similarities characterize Stch as a constitutively expressed member of the stress70 family. Although the molecular basis for the two Stch transcripts is unknown, we demonstrated that non-overlapping cDNA probes from the 5' (nucleotide co-ordinates #57–413, SEQ ID NO:5), middle (co-ordinates #364–1155, SEQ ID NO:3) and 3' untranslated (co-ordinates #1533–2025, SEQ ID NO:6) portions of human Stch detected both 4.4 and 2.4 kb transcripts in RNA extracted from human tumor cell lines suggesting that both the 4.4 and the 2.4 kb transcripts encode Stch specific sequences.

E. Localization of Stch to Chromosome 21

The genomic Stch clone was obtained by screening a commercially available human genomic library (#946205, Male Caucasian Fetus placenta packaged into Lambda FIX II vector, Stratagene) with a Stch cDNA probe obtained by polymerase chain amplification of a segment of Stch cDNA (SEQ ID NO:1). The amplified segment was obtained from position 67 to position 504 (SEQ ID NO:22) using oligo primers SEQ ID NO:17 and SEQ ID NO:18. This probe was used in a genomic library to obtain a genomic clone. The clone identified by probe hybridization was a 8.5 kb sequence having at its 3' end the sequence equivalent of SEQ ID NO:22. This genomic probe contains promoter elements and was incoprorated into a γ FIX II vector. Fluorescent in situ hybridization was performed using SEQ ID NO:22. The fluorescence in situ hybridization was performed by Paragon Biotech, Inc. (Baltimore, Md.) at their contract facility. Fluorescent in situ hybridization studies were performed using biotinylated probe that hybridized to human metaphase chromosomes. 150 ng, 225 ng and 232 ng of labelled probe were used for the hybridization. Forty-five metaphase spreads were analyzed and results indicated that Stch labelled both chromatids of each long arm of chromosome 21. Fluorescent in situ hybridization is known in the art and methods for performing this technique are readily available. Those with skill in the art recognize that contract facilities are similarly available to perform these services. Therefore, no further description is required to enable those with skill in the art to employ SEQ ID NO:22 to identify a genomic clone from a human genome library and to use the genomic sequence from the clone as a probe to localize Stch to the human genome. The Stch gene localized to chromosome 21q. Therefore STCH probes are useful for detecting chromosome 21 and in particular for identifying the chromosome 21q location.

The chromosome location of Stch was confirmed by PCR amplification of genomic DNA from somatic cell hybrids (BIOS Laboratories, Inc.). Amplified fragments from SEQ ID NO:19 and SEQ ID NO: 20 were obtained from the somatic cell hybrids and were transferred to nitrocellulose and probed with SEQ ID NO:21 that had been end-labelled with $\gamma[^{32}P]$-ATP using T4 polynucleotide kinase. A description of the somatic cell hybridization methods is detailed in Example II.

CHARACTERIZATION OF THE STCH PROTEIN

A. Preparation and Purification of Antibodies to STCH

Preferred methods for vector construction, STCH expression and immunization are provided in Example III. Those with skill in the art of immunology and molecular biology will readily recognize that a variety of methods for constructing and expressing genes, or gene fragments, in either eukaryotic or procaryotic expression systems are known in the art and that these variations do not detract from the scope of this invention. Moreover, those skilled in the art will recognize that the recombinant nucleic acid of SEQ ID NO: 1 or SEQ ID NO: 13 or recombinant or synthetic nucleic acid molecules of at least 30 consecutive nucleotides in length can be readily incorporated into a variety of vectors, both eukaryotic and prokaryotic, and that vector selection will in part, determine whether the vectors encode protein or protein fragments from SEQ ID NO: 1 or SEQ ID NO: 13. Those skilled in the art will be able to select the appropriate vector for their particular application. Exemplary gene vectors are employed and discussed throughout this text. For purposes of this invention, the term "polypeptide" is used interchangeably with the term "protein".

It is also well know in the art that commercially available kits permit the incorporation of gene sequences encoding protein into prokaryotic and eukaryotic vectors without undue experimentation. Further, these kits enable those even modestly skilled in the art to transform or transfect prokaryotic and eukaryotic cells respectively. Therefore, this invention additionally contemplates eukaryotic and prokaryotic cells containing recombinant or synthetic nucleic acid molecules consisting essentially of SEQ ID NO: 1 or SEQ ID NO: 13, recombinant homologs and recombinant or synthetic nucleic acid molecules of at least 30 consecutive nucleotides in length.

Example III provides a preferred method for producing STCH protein and Tables I and II (supra) provide 2 STCH protein sequences from human and rat genomes respectively. Thus, this invention provides a method for making recombinant polypeptide encoded by SEQ ID NO: 1 or SEQ ID NO: 13 that comprises introducing a gene vector capable of directing polypeptide expression that contains at least 30 sequential nucleotides from SEQ ID NO: 1 or SEQ ID NO: 13 into a host cell, expressing the polypeptide, isolating the polypeptide and purifying the polypeptide. A variety of methods are well recognized in the art for producing recombinant protein. Commercial systems are available from Pharmacia, Stratagene, Invitrogen, or the like, to express, isolate and purify recombinant protein from either eukaryotic or prokaryotic cells. These variations do not detract from the present invention. STCH polypeptide fragments were produced and described as detailed in Example IV. In addition, synthetic peptide synthesis permits those skilled in the art to produce synthetic peptides consisting of at least 15 consecutive amino acids from SEQ ID NO: 2 or SEQ ID NO: 14. Such peptides can be readily synthesized by those skilled in the art and also are contemplated in the present invention.

Antibodies specific to STCH were prepared in rabbits. As one method for generating specific antibodies to STCH, expression vectors encoding distinct STCH domains from glutathione S-transferase (GST)-STCH fusion proteins were prepared and the GST-STCH proteins were expressed in E. coli. Gene fragments were amplified from the full length cDNA clone using 2 pairs of PCR primers. The first domain incorporated into the GST fusion vector was nucleotides 349 to 504 of SEQ ID NO:1, coding for residues 105–156 of SEQ ID NO:2 (SEQ ID NO:7) The domain was amplified from the full length clone using the two PCR primers SEQ ID NO:8 and SEQ ID NO:9. The second domain incorporated into the GST fusion vector was nucleotides 817 to 1221 of SEQ ID NO:1, coding for residues 261–395 of SEQ ID NO:2 (SEQ ID NO:10). The second domain was amplified using SEQ ID NO:11 and SEQ ID NO:12. The vectors were transformed into E. coli and the expression products were isolated and used as immunogen for STCH-specific antibody production. The human Stch gene was subcloned by cloning blunted SmaI-HindIII fragments into the SmaI site of pGEX-3 (Pharmacia) giving an in-frame sense oriented fusion protein. The supernatant was incubated with glutathione agarose beads (Pharmacia). A complete method for antibody production is detailed in Example III. It is further contemplated that other polypeptide fragments can be used to produce antibody to STCH. Thus, polypeptide of at least 15 consecutive amino acids from SEQ ID NO: 2 can be used as immunogen to produce either polyclonal or monoclonal antibody. These antibodies specifically recognize at least 15 consecutive amino acids from SEQ ID NO: 2. The results indicated that polypeptide domains from STCH had restricted homology to HSP70 and BiP.

Antisera harvested from the immunized animals were pre-absorbed over glutathione—Sepharose beads (Pharmacia, Piscataway, N.J.) linked to the GST leader peptide to purify the antibodies before use and to reduce non-specific reactivity. The pre-cleared α-STCH antisera was used to immunoprecipitate [$^{35}$S]methionine-labeled H2172 cell (patient derived non-small cell carcinoma cell) lysates. Antibodies specific for STCH from other species, such as mice and rats, are also contemplated in this invention. Those with skill in the art of immunology will recognize that the immunogen injected into rabbits can similarly be injected into rats and mice. These methods are well known in the art. Like the rabbit sera, polyclonal antibodies can similarly be purified from the rat and mice sera. Monoclonal antibodies are also contemplated in this invention. Since STCH is immunogenic and since polyclonal antibody has been isolated, those with skill in the art can readily make monoclonal antibodyto STCH without undue experimentation. A preferred monoclonal antibody strategy is disclosed in Example III.

Antibody fragments (either Fab or F(ab')$_2$) are contemplated in this invention. Methods for producing Fab or F(ab')$_2$ fragments are well known in the art and strategies for creating antibody fragments are discussed by Philps, J. L., et al. (J. Immunology. 145: 1200–1204, 1990 which is hereby incorporated by reference).

B. Immunoprecipitation of the Human STCH Product

To detect the presence of STCH protein in human cells, a cell sample from a patient was washed and lysed in a nonionic detergent such as non-idet p-40 (NP-40). The supernatants were clarified by centrifugation either using labelled antibody or radio-labelled cell lysates (such as a [$^{35}$S]methionine-label) and the antibody/antigen complexes were precipitated with Protein A-Sepharose CL-4B (Pharmacia). The precipitates were washed and subjected to sodium dodecyl sulphate-polyacrylamide gel electrophoresis (SDS-PAGE). The results indicated that STCH migrated on SDS-PAGE predominantly as a 60 kDa species, although a 72 kDa band was also observed. The results were confirmed using polyclonal antisera isolated from different animals which also gave similar results. In contrast, precipitation reactions using pre-immune sera resulted in non-specific banding patterns void of either the 60 kDa or 72 kDa protein species.

The specificity of the antibody to the STCH protein was confirmed using polyclonal antibodies preabsorbed with either one or both of the GST-fusion products. In this experiment, the polyclonal antibodies were preabsorbed over glutathione—Sepharose beads linked to the GST leader sequence, GST—peptide 1 and 2, GST—peptide 1 (SEQ ID NO: 7), or GST—peptide 2 (SEQ ID NO: 10) (see Example IV). Peptide 1, but not peptide 2 or the GST leader peptide, competed for specific binding to the 60 and 72 kDa bands. This experiment confirmed the specificity of the α-STCH antisera for the STCH peptide 1 domain and for the 60 and 72 kDa products. Size predictions based on the Stch gene sequence suggested that STCH should migrate as a 60 kDa protein. Since the p72 species seen on immunoprecipitation studies is significantly larger than that predicted by the Stch cDNA, p72 may represent another HSP70-related protein that contains an epitope similar to STCH peptide 1. However, antisera raised to STCH does not recognize other members of the stress70 protein family such as HSP70 and BiP. p72 could represent the product of an alternatively spliced Stch transcript; however, a Stch cDNA has not been isolated that represents an alternative open reading frame.

C. Immunoassays for STCH Detection and Cell Localization

Double-labeling immunofluorescence was performed on preparations of HeLa cells utilizing α-STCH antisera (preabsorbed over the GST leader peptide) tagged with fluorescein and either α-BiP or α-HSP70 tagged with Texas Red. These experiments localized STCH to the cellular cytoplasm in a pattern that resembled, but was not identical to, the ER staining of BiP and was distinct from the HSP70 cell staining pattern. Specificity of the α-STCH polyclonal antibodies was confirmed by the absence of cytoplasmic staining with polyclonal antibodies pre-absorbed with STCH peptide 1.

To further define the subcellular localization of STCH, microsome preparations from 5×10$^8$ K562 cells (erythroleukemia cells) were prepared by centrifugation of cell homogenates over non-continuous sucrose gradients as described by Tartakoff, et al. (J. Cell. Biol. 83: 284–299, 1979) and disclosed in Example IV. 50 µg of protein from the subcellular fractions as well as 50 µg of whole cell protein (representing—10$^6$ cells) were employed in an immunoblot analysis with the α-STCH polyclonal antibodies. The results of this fractionation demonstrated that STCH was enriched in the denser microsome fraction isolated at the 1.3M/1.2M sucrose interface. In contrast, STCH levels were significantly reduced in the washed nuclear pellet and in the lighter microsome fraction harvested at the 1.2M/0.5M sucrose interface. These experiments also indicated that the α-STCH antibodies react with the 72 kDa species in immunoblot assays and that p72 fractionated with p60. The p72 species specifically reacted with antibody to the STCH peptide 1 epitope. Although it remains possible that the p72 species may represent the product of an alternatively spliced Stch mRNA, such a transcript was not isolated. p72 could represent a distinct HSP70-like molecule that shares sufficient homology with STCH to allow reactivity with the antibodies specific to STCH. Neither BiP nor HSP70 showed cross-reactivity to antibodies specific to STCH.

The subcellular fractionation was repeated and equal amounts of the whole-cell protein lysate or the denser microsome fraction were subjected to immunoblot analysis in triplicate. The nitrocellulose filter was divided in half and probed with either α-HSP70, α-STCH or α-BiP. This experiment demonstrated that the 60 and 72 kDa species recognized by the α-STCH antisera did not co-migrate or cross-react with either human HSP70 or human BiP, and confirmed that, in contrast to the cytosolic HSP70 protein, STCH appeared to be more highly enriched in the microsome fraction than BiP. This suggested that BiP may be released during the microsome preparation or that both proteins are localized in different subcellular compartments.

To determine whether STCH is peripherally associated with the outer membrane or localized to the lumen of microsomes, a protease digestion experiment was performed in the presence or absence of detergent (Triton X-100). A preferred method for performing protease digestion assays is provided in Example V. The STCH product obtained from the dense microsome fraction of a discontinuous sucrose gradient was susceptible to protease digestion only after solubilization of the membranes with mild detergent. This is consistent with an intraorganellar localization of the STCH product.

FUNCTIONAL CHARACTERISTICS OF STCH

A. STCH Demonstrates Peptide-independent ATPase Activity

Inspection of the primary amino acid sequence of the STCH product predicts a functional ATPase molecule. ATPase activity was tested using a GST -Stch plasmid that encoded a functional fusion protein including STCH codons 4–471 (See Table II and SEQ ID NO: 1). A preferred strategy for preparing this fusion protein is provided in Example III and a preferred strategy for performing ATPase assays is provided in Example VI. To exclude contaminating sources of ATPase, the GST leader peptide and the GST-STCH affinity-purified fusion proteins were eluted off glutathione—Sepharose beads, then purified by anion-exchange chromatography (mono Q) and the protein composition of the column fractions was analyzed by SDS—PAGE. The peak ATPase activity of the GST —STCH product coincided with fractions 11 and 12. While no measurable ATPase activity was detected in fractions 11 and 12 from the GST leader sequence. These fractions were pooled from the GST—STCH sample and ATPase activity was measured in the presence or absence of two different peptides. This data was compared with purified BiP and with the bacterial HSP70, dnaK. In contrast to BiP (Flynn et al., 1989, supra) and dnaK, and as predicted from the structural analysis predicting a truncated carboxyl terminus, STCH did not exhibit a peptide-stimulated enhancement of ATPase activity. The $K_m$ for the unstimulated STCH ATPase was 2–3 μM ATP and the measured ATPase activity was linear with respect to time and concentration over the range tested.

Thus, analysis of the novel stress70 gene Stch indicates that the protein has functional features that characterize it as a chaperone protein. Stch has a number of functional similarities to the ER lumenal protein BiP, including constitutive expression in human tissues and mRNA induction following cell incubation with the calcium ionophore A23187. This pattern suggests that the protein STCH has a function associated with calcium ion fluxes in a membrane-based compartment. Consistent with this prediction, we observed that STCH contains a 22 residue hydrophobic leader peptide. This leader peptide also has some similarities to the GRP78/BiP signal sequence since both STCH and BiP have an N-terminal hydrophobic amino acid sequence. Moreover, like Bip, STCH localizes to the lumen of microsome membranes. However, unlike BiP, STCH does not encode a consensus ER retention signal. Most ER proteins encode retention or retrieval sequences at their C-terminus. The characteristic sequence is a C-terminal KDEL sequence or a KKXX sequence where X represents any amino acid. Both C-terminal motif sequences are observed in ER proteins. The KTNFN C-terminal sequence of human and rat STCH seems to be another microsomal compartment targeting sequence.

In summary, inspection of the STCH amino acid sequence revealed a protein that is predicted to encode a "core ATPase" molecule that has been observed in HSC70 and BiP. However, in both HSP70 and BiP, the core ATPase activity was observed only after the proteolytic cleavage of the HSC70 or BiP products in vitro. The amino acid sequence of STCH is quite different from HSC70 and BiP. The STCH amino acid sequence has about a 33% identity to human HSP70 and a 43% homology to human BiP. HSC70 and HSP70 share a 95% homology. The similarities to BiP and HSP70 are localized within the five ATP-binding/hydrolysis consensus domains and their immediate flanking regions.

Unlike either HSP70 or BiP, STCH contains a 50 residue insertion within the ATP-binding domain between the phosphate2 and adenosine ATP-binding sequence motifs and has truncated carboxyl terminal peptide-binding sequences just downstream of the last consensus ATP-binding domain. Both HSC70 and BiP include a transient 60 kDa species followed by the accumulation of a 44 kDa N-terminal fragment. Like the digestion products of HSC70, STCH terminates two residues downstream of a hypothetical cleavage site for the 44 kDa N-terminal fragment of HSC70. In vivo immunoprecipitation, detects a 60 kDa STCH protein. If STCH is the structural and functional analog of the 44 kDa fragment, the discrepancy in size may be explained in part by conformational changes induced by the amino acid insertion within the STCH molecule.

Since the three-dimensional structure of the N-terminal fragment of HSC70 has been recently published, we determined the predicted location of the 50 residue insertion within the STCH molecule and observed that it was outside of the ATP-binding pocket within the HSC70 protein-folding domain, IIb. To examine directly whether ATPase activity would be affected by this insertion or by the absence of a carboxyl terminal domain, we assayed for enzyme activity using purified BiP, dnaK and a recombinant STCH product representing codons 4–471. In contrast to BiP and dnaK, STCH exhibited ATPase activity that was independent of peptide stimulation. STCH, therefore, is functionally equivalent to the "ATPase core" of bovine HSC70 which retained ATPase activity that was uncoupled from a dependence on clathrin binding. We have, therefore, identified an in vivo HSP70-related molecule with properties similar to the in vitro proteolytic HSC70 fragment. This suggests a unique role for STCH in protein processing. For example, these features indicate that STCH may represent a calcium inducible ATPase molecule that reversibly binds to a subunit or family of subunits that functions to both confer peptide specificity and to regulate its ATPase activity. These proteins have been isolated by precipitating [$^{35}$S]-methionine labeled rat cell lysates with the recombinant rat protein STCH. The precipitated protein is visualized by SDS-PAGE electrophoresis and autoradiography.

A number of methods are set forth as part of this invention. For example, methods are disclosed for making recombinant polypeptide encoded by SEQ ID NO: 1 or SEQ ID NO: 13. Example III illustrates one embodiment for the method of introducing a gene vector capable of encoding a polypeptide, wherein the polypeptide consists of at least 30 sequential nucleotides from SEQ ID NO: 1 or SEQ ID NO: 13, into a host cell, expressing the polypeptide in the cell, isolating the polypeptide and purifying the polypeptide.

Methods have been provided for detecting Stch transcripts in a tissue sample. A "tissue sample" includes a tissue biopsy or a cell sample expanded in culture prior to testing for Stch transcripts. Example II illustrates an exemplary method for detecting Stch in a cell genome. Methods have been disclosed for detecting the presence of STCH protein in a cell sample. Exemplary immunoprecipitation, immunoblot, immunofluorescent and ELISA assays are provided in Example IV. It is contemplated that those skilled in the art will know how to determine the specificity of an antibody and will therefore know how to determine the specificity of an antibody produced in response to STCH immunogen. As one method for determining the specificity of STCH, cell samples that are known to contain STCH protein are lysed and separated by SDS-PAGE and transferred to an immobilizing membrane such as nitrocellulose or the like and incubated with STCH antibody as a Western Blot. Methods for performing Western Blots are also well known in the art (see Davis, et al. supra). The presence of STCH antibody is detected by a second incubation using a secondary antibody conjugated to immunoperoxidase, or the like. Finally, assays and methods are disclosed to detect ATP in a sample and to assess the ATPase activity of STCH are provided in Example VI.

STCH has a number of characteristics that indicate the protein is analogous to BiP. Therefore STCH is useful as a folding-promoting agent. It is contemplated that STCH can be added to a sample to promote protein folding during in vitro translations (see Example VIII or to promote protein folding after urea denaturation or for x-ray crystallography). Finally, this invention identifies two novel leader sequences that direct protein to the microsomal lumen important for protein processing. It is know in the art, that once leader sequences are identified, they can be incorporated into their expression vectors to direct the expression of other protein to their correct subcellular compartments. Art exemplary use of the leader sequence is provided in Example IX.

Particular embodiments of the invention will be discussed in detail and reference will be made to possible variations within the scope of the invention. There are a variety of alternative techniques and procedures available to those of skill in the art which would similarly permit one to successfully perform the intended invention.

EXAMPLE 1 cDNA Cloning and Sequencing

Cell lines and propagation

K562 erythroleukemia cells and HeLa cells were obtained from the American Type Culture Collection (Rockville, Md.), and the H2009 and H2172 cell lines were derived from patients with non-small cell lung cancer. All cell lines were propagated at 37° C./6% $CO_2$ in RPMI media supplemented with 10% fetal calf serum.

cDNA cloning and sequencing

The initial STCH cDNA clone was obtained by screening a K562 λgt11 library with a [$^{32}$P]dCTP random primed probe corresponding to the retinoblastoma binding protein-1 gene (Otterson et al., 1993, supra). Overlapping cDNA clones were subsequently obtained by screening a KB62λgt11 library and an H69 Uni-ZAP library (Stratagene, La Jolla, Calif.) with a [$^{32}$P]dCTP random primed probe derived from the partial Stch cDNA clone (pStch1; nucleotide co-ordinates; #364–1155 SEQ ID NO: 3). Hybridization and washing conditions for the library screenings were as previously described (Davis et al., Basic Methods in Molecular Biology, pp. 68–83 Elsevier Press, NY1986). pStch1 was nick translated using α $^{32}$P-dCTP (NEN) according to the method of Davis, et al. (pg 81, supra) which is hereby incorporated by reference. Briefly, 0.5 µg of pStch1 in 7 µl $H_2O$ was added with 0.5 µl DNaseI, 4 µl unlabeled triphosphate mix (200 µM dGTP, clATP and dTPP) 2.5 µl nick translation buffer (0.5M Tris, pH 7.4, 0.1M MgSO4, 1 mM DTT, 500 µg/ml BSA, Pentax Fraction V (Sigma) and 10 µl of α-$^{32}$P-dCTP (at a final concentration of 1–2 µM). The reaction was incubated at 14° C. for 20 minutes. The probe was purified by phenol/chloroform extraction and activity was quantitated by trichloroacetic acid precipitation.

DNA samples from colony hybridizations or from DNA dot blots or RNA blotted onto nitrocellulose were screened for the presence of Stch DNA or RNA using Southern or Northern hybridization conditions respectively. The Southern blots were hybridized and prehybridized in 10 ml buffer-N. (80 g Dextran Sulfate, 300 ml $H_2O$, 320 ml deionized formamide, 160 ml 20×SSC buffer, 2.8 ml 2M Tris, pH 7.4, 8 ml 100×Denhardts and 8 ml of 2 mg/ml salmon sperm DNA for 800 ml). Filters were washed in 500 ml of wash solution A (200 ml 20×SSC, 1780 ml $H_2O$ and 20 ml 10% SDS) and solution B (10 ml 20×SSC, 1970 ml $H_2O$ and 20 ml 10% SDS). 1 liter of 20×SSC was prepared using 175.3 g 3M NaCl, 88.2 g 0.3M $Na_3Citrate.2H_2O$ in 800 ml $H_2O$ with the pH adjusted to 7.0.

For sequencing, positive cDNA inserts were subcloned into the pT7 vector (Novagen, Madison, Wis.) and subjected to dideoxynucleotide sequencing using a kit supplied by the manufacturer (US Biochemical, Cleveland, Ohio). Additional 5' sequence was obtained using an anchored PCR kit as described by the manufacturer (5'RACE kit, Life Technologies, Gaithersburg, Md.). The nucleotide sequence was confirmed from at least two independent products.

In addition, the Stch sequence was confirmed using independent cell lines H2172 and H2009 as sources of cDNA. The nucleotide position 1274–2027 of SEQ ID NO:1 was confirmed using SEQ ID NO:23 and SEQ ID NO:24 in a PCR reaction using the conditions described above. This region was of particular interest because the TAG stop signal is positioned in a location unique to STCH and different from other stress70 chaperone proteins.

EXAMPLE II

Nucleic Acid Analysis

Determination of Stch Gene Copy Number

Ten micrograms of genomic DNA from human, rat and Drosophila tissues were digested to completion with either BamHI or EcoRI (Life Technologies), and subjected to Southern blot analysis as described by Davis, et al (supra) using the $^{32}$P-labeled pStch1 cDNA probe. Approximately 2×10$^7$ c.p.m. of radiolabeled probe were incubated overnight with the blotted nitrocellulose membrane in 10% dextran, 4×SSC, 40% formamide, 1×Denhardt's, 20 µg/ml herring sperm DNA, and 20 mM Tris (pH 7.4) at 37° C. Filters were washed sequentially in 2×SSC, 0.1% SDS and 0.1×SSC, 0.1% SDS at 37° C., followed by autoradiography. STCH was present as a single locus in human and rat tissue.

Two micrograms of poly(A)$^+$ RNA extracted from human heart, brain, placenta, lung, liver, skeletal muscle, kidney and pancreas tissues were size fractionated on a formaldehyde/agarose gel and transferred to a nylon membrane (Clontech, Palo Alto, Calif.) which was hybridized overnight with the $^{32}$P-labeled pStch1 probe at 42° C. in the hybridization buffer described above and washed at 50° C. in the wash solutions described above. Stch was identified in each tissue tested.

Localization of Stch to Chromosome 21

Two microliters of genomic DNA (50 micrograms per microliter) were used as template in PCR reactions of 50 microliters each using 200 micromolar concentration of SEQ ID NO:19 and SEQ ID NO:20. Reaction conditions were 95° C. for 1 minute followed by an annealing at 58° C. for 1 minute and extension at 72° C. for 2 minutes. This was repeated for 30 cycles. Ten microliters of the reaction mixes were then size fractionated on a 1% agarose gel and visualized with Ethidium Bromide under ultraviolet irradiation. The DNA was transferred to nitrocellulose by Southern transfer (Davis, et al. supra) and hybridized overnight with SEQ ID NO:21 end labelled with γ[$^{32}$P]-ATP. The nitrocellulose was prehybridized with a hybridization solution containing 10% dextran sulfate, 6×SSC (0.9M NaCl, 0.09M NaCitrate), 1% (w/v) SDS, 5×Denhardt's solution (0.1% polyvinylpyrrolidone, 0.1% ficoll, 0.1% bovine serum albumin), 100 µg denatured salmon sperm DNA/ml at 65° C. for 30 minutes. The nitrocellulose was hybridized with fresh hybridization solution overnight with labelled probe. The nitrocellulose was rinsed in 0.5×SSC, 0.5% SDS for 10 minutes at room temperature followed by washes at 65° C. with preheated 0.5×SSC, 0.5% SDS with gentle agitation. Those lanes representing different somatic cell hybrid genomes containing Stch had positive bands by autoradiography. Discordance tables and analysis guidelines were provided by BIOS Laboratories and are available in the BIOSMAP™ Somatic Cell Hybrid Test Kit. Discordance analysis confirmed the location of Stch to Chromosome 21.

Heat Shock and Calcium Ionophore Induction Analysis

A total of 3×10$^6$ cells were subjected to heat shock (44° C. for 2 h) or to the calcium ionophore A23187 (Calbiochem, San Diego, Calif.) and total RNA was harvested by guanidine isothiocyanate extraction (Chirgwin et al., *Biochemistry* 18: 5294–5299, 1979). Ten micrograms of RNA from each sample were size fractionated on a formaldehyde/agarose gel and transferred to nitrocellulose, followed by hybridization with the $^{32}$P-labeled pStch1 probe or the Hsp70 cDNA probe, pH2.3 (Hunt, et al., 1985 supra), and autoradiography. The pH2.3 probe was obtained from the full cDNA sequence of human hsp70 by digesting the hsp70 sequence with the restriction endonuclease BglII which cuts at nucleotide positions 841 and 1765 releasing a 921 base pair fragment from the parent cDNA. Ethidium bromide staining of the 28S and 18S rRNA subunits was evaluated to confirm the amount and integrity of RNA loaded.

In contrast to HSP70, Stch was not inducible by heat shock; however, steady-state levels were enhanced following 24 h treatment of cells with the calcium ionophore A23187.

EXAMPLE III

Production of α-STCH Antisera

To generate STCH-specific antisera, STCH fusion proteins were produced peptide 1 (SEQ ID NO:7) containing residues 105–156 of SEQ ID NO:2, and peptide 2 (SEQ ID NO:10), containing residues 261–395 of SEQ ID NO:2; both exhibited reduced homology to other previously reported stress70 proteins. Oligonucleotide pairs for DNA encoding peptide 1, sense: 5'-GGATCCGGCAAGATTTTTACCGCAGAAGAG-3' (SEQ ID NO: 8) and antisense: 5'-GGATCCTTACTTTAACTTCAACAATAGTCGAGA-3' (SEQ ID NO: 9); and for DNA encoding peptide 2, sense: 5'-GGATCCAGATTGCTTCAGTACTTATATAAACAG-3' (SEQ ID NO: 11) and antisense: 5'-GGATCCTTAGTGGCCTTCTTTCAATACTTGCTG-3' (SEQ ID NO: 12), were designed to subclone PCR products in-frame into the BamHI site of the bacterial expression plasmid pGEX2T (Pharmacia). The nucleotide sequence of the fusion expression vectors was confirmed and GST-STCH fusion proteins were produced as previously described (Smith, et al., 1988) and detailed below.

The screening of transformants for expression of fusion protein was conveniently carried out on 1.5 ml of culture pelleted and resuspended After sonication and centrifugation, the supernatant was mixed with 50 µl of 50% glutathione-agarose beads, washed with 3×1 ml NETN and the beads were boiled in 100-µl sample buffer for analysis on a 0.1% SDS-10% polyacrylamide gel followed by staining with 0.05% Coomassie blue.

Fusion protein was purified by growing overnight cultures of *E. coli* HB101 transformed with the desired GST plasmid. The cultures were diluted 1:10 in 800 ml of fresh medium and grown for 1 h in LB media containing 50 µg/ml ampicillin. After one hour of growth, isopropyl-β-D-thiogalactopyranoside (IPTG) was added to a final concentration of 0.1 mM. Cultures were allowed to grow with vigorous shaking for an additional 3–4 hours. Cells were pelleted by centrifugation at 2500×g for 5 min at 4° C. and resuspended in NETN buffer (20 mM Tris pH 7.6, 100 mM NaCl, 1 mM EDTA, 0.5% NP40, with 1 mM PMSF). Cells were lysed on ice by mild sonication and centrifuged at 10,0000×g for 5 min at 4° C. The supernatant was mixed at 4° C. in a 50-ml polypropylene tube on a rocking platform for 30–60 minutes with 50 µl of glutathione-Sepharose (Sigma, St. Louis, Mo.) that had previously been washed 3 times and resuspended in 1:1 (v/v) in NETN containing 0.5% powdered milk. The beads were collected by brief centrifugation at 500×g and washed three times with NETN. Fusion protein was eluted by competition with free glutathione using 2×2-min washes with 1 bead volume of 50 mM Tris HCl (pH 8.0) containing 5 mM reduced glutathione (Sigma) (final pH 7.5, freshly prepared). The yield of unstable fusion proteins was increased by delaying the addition of IPTG until less than one hour before cell harvest. Glutathione-agarose beads have a capacity of at least 8 mg of fusion protein/ml of swollen beads. For a modified procedure see Smith, et al. (*Gene* 67:31–40, 1988).

Yields of fusion protein were calculated from the absorbance at 280 nm using the relation 1 $A_{280}$=0.5 mg/ml derived from protein concentration estimations of protein purified from cells transformed with pGEX-1 and using bovine serum albumin as a standard.

Approximately 1 mg of freshly purified fusion proteins (GST-STCH peptides 1 and 2) was mixed with an equal amount of Freund's adjuvant and injected intramuscularly into two New Zealand White rabbits three times over a 6 week period. Polyclonal antibodies were isolated from the antisera by preabsorbing the antisera four times over glutathione-Sepharose attached to the GST leader peptide. Antibodies were also pre-absorbed over GST-STCH peptides 1 and 2.

Monoclonal Antibody Production

The STCH protein, purified as described in the preceding paragraph, is used to immunize rats. A Fisher rat is immunized five times, every third day, in one rear foot pad with the antigen. The first injection of immunogen is emulsified in incomplete Freund's adjuvant and others are administered in phosphate-buffered saline (PBS). One day after the last injection, the draining popliteal lymph node is fused with mouse myeloma Ag8.653 (Kearney, et al. *J. Immunol.* 123: 1548–1550, 1979 which is hereby incorporated by reference). Hybridomas are initially screened by an enzyme-linked immunosorbent assay (ELISA) for reactivity against STCH. An exemplary ELISA assay is provided in Example IV. The hybridomas secreting antibody specific for STCH by enzyme-linked immunosorbent assay are further screened for their ability to immunoprecipitate STCH from a labeled cell lysate as detected by SDS-PAGE.

EXAMPLE IV

Detection of STCH in Cell Samples

Immunoprecipitation

A total of $3\times10^6$ H2172 cells were washed and pre-incubated for 1 h in RPMI minus methionine media (Gibco, Grand Island, N.Y.) and then supplemented with 100 μCi/ml [$^{32}$S]methionine (Amersham Life Sciences, Arlington Heights, Ill.) for 3 h at 37° C. Labeled cells were washed with phosphate-buffered saline (PBS) and lysed in buffer [50 mM Tris-HCl (pH 7.4), 250 mM NaCl, 50 mM NaF, 0.1% NP-40 supplemented with 1 mM phenylmethylsulfonylflouride (PMSF)]. The supernatant was clarified by centrifugation at 14,000 r.p.m. at 4° C. for 5 min and used directly for immunoprecipitation. [$^{32}$S]Methionine-labeled cell lysates were incubated with either α-STCH antisera or STCH-sera pre-absorbed with different immunizing peptides for 1 hour at 4° C., followed by a 1 hour incubation with washed protein A-Sepharose CL-4B (Pharmacia). The immune precipitates were washed five times in lysis buffer and subjected to SDS-PAGE and autoradiography.

Immunoblot Assays

For immunoblot analyses, unlabeled cells were lysed as described above and equal amounts of protein were size fractionated by 7.5% SDS-PAGE, transferred to nitrocellulose and incubated overnight with α-STCH antisera at a 1:200 dilution, or with α-BiP or α-HSP70 (StressGen, Victoria, BC) as directed by the manufacturer. Filters were washed and exposed to [$^{125}$I]Protein A (Amersham) for 90 min, followed by autoradiography.

Immunofluorescence Assays

Approximately $2.5\times10^4$ HeLa cells were split into 8-multichamber glass slides and allowed to grow for 24 h. The cells were fixed in 4% paraformaldehyde for 30 min, permeabilized in 0.5% Triton X-100 for 10 min and blocked for 30 min in 4% bovine serum albumin (BSA) in PBS (all subsequent dilutions were prepared in this solution). Polyclonal α-STCH antibodies were incubated at a 1:10 dilution for 2 h, followed by a 30 min incubation with a 1:20 dilution of swine-derived α-rabbit antibody conjugated to fluorescein (Dako, Carpinteria, Calif.). Monoclonal antibodies to BiP and HSP70 (StressGen, city, state) were diluted 1:100 and incubated for 30 min, followed by a 30 min incubation with a 1:50 dilution of goat α-mouse antibody conjugated to Texas Red (Oncogene Science, Uniondale, N.Y.). All incubations were performed sequentially at room temperature and in the dark, following the initial application of fluorescent conjugates. The specimens were examined with a Zeiss fluorescent microscope.

ELISA Assay to Detect STCH in a Sample 96-well microtiter plate are coated with antibody to STCH. Plates are incubated overnight at 4° C. at an antibody concentration of 100 μl/well in sodium carbonate buffer pH 9.6. Plates are washed in PBS three times and incubated with 1% BSA in PBS for 1 hour at room temperature. The plates are washed with PBS 6 times. 100 ul cell sample cytosols and standards are dispensed into the wells followed by RT incubation for 2 hours with gentle agitation. The plates are washed with PBS 6 times. 100 μl/well of a second set of anti-STCH antibodies preferably monoclonal, labelled with horseradish peroxidase are added to the wells for 1 hour at RT. Again, plates are washed with PBS 6 times. 100 μl/well of orthophenylene diamine (OPD) solution is added and the plates are incubated in the dark at RT for 15 minutes. The reaction is stopped by adding 100 μl/well sulfuric acid and the absorbance is recorded at 490 nm. Standard curves are constructed by plotting absorbance against standard STCH concentrations. The STCH concentration in test samples is calculated by interpolation of absorbance on the standard curve.

EXAMPLE V

Cell Localization of STCH Using Protease Digestion Assay

Subcellular fractionation

To prepare subcellular fractions for immunoblotting analysis, $5\times10^8$ K562 cells were resuspended in 10 mM Tris-HCl (pH 7.4), 10 mM KCl, 1.5 mM $MgCl_2$ on ice for 10 min. Cell membranes were then disrupted by 15 strokes with a Dounce homogenizer and centrifuged at 1000 g for 5 min. The nuclear fraction (pellet) was washed in TKM [50 mM Tris-HCl (pH 7.4), 100 mM KCl, 5 mM $MgCl_2$] and resuspended in lysis buffer. The supernatant was made isotonic with TKM and a 2×solution of 2.4M sucrose in TKM was added for a final concentration of 1.2M sucrose (see Tartakoff, et al., 1979 supra). A non-continuous sucrose gradient was prepared using successive layers of 2.0M sucrose, 1.3M sucrose, post-nuclear supernatant in 1.2M sucrose, 0.5M sucrose and TKM. The sucrose gradient was then centrifuged at 50,000 r.p.m. in an SW 50.1 rotor (Beckman, Palo Alto, Calif.) for 18 h. The 1.3M sucrose/ 1.2M sucrose interface and the 1.2M sucrose/0.5M sucrose interface were diluted to 5 ml in TKM and spun for 1 h at 50,000 r.p.m. in the SW 50.1 rotor. The pellets, representing a crude microsome preparation, were resuspended in lysis buffer and used for immunoblotting analyses as described in the previous example. 50 μg of protein from whole-cell lysates, the nuclear pellet, the 1.3M sucrose/1.2M sucrose interface pellets (1.3M/1.2M), or the 1.2M sucrose/0.5M sucrose interface pellets (1.2M/0.5M) were subjected to immunoblotting with the α-STCH antisera. Immunoblot analysis compared 50 μg of protein from K562 whole-cell lysates (WCL) or microsome preparations for STCH, HSP70 and BiP protein expression.

Microsome membrane preparations from K562 cells were prepared as described above. The membrane aliquots (15 μl) were incubated for 5 min with or without 1% Triton X-100 prior to the addition of 0.3 μg proteinase K (Boehringer Mannheim). The reaction was stopped after 10 min at 30° C. to allow protease digestion to occur with the addition of 1 mM PMSF. Control reactions without added protease were also performed. Samples were analyzed by SDS-PAGE (10% acrylamide), followed by immunoblotting with the α-STCH antibodies as described above.

EXAMPLE VI

ATPase Activity of STCH

A GST leader peptide and a near full-length GST-STCH fusion protein, representing STCH codons 4–471, were purified from bacterial proteins using glutathione-Sepharose beads as described previously (Example III and Smith, et al. (1988 supra). The proteins were released from the beads by incubation with 5 mM reduced glutathione in 50 mM Tris (pH 8.0), 1 mM DTT, for 10 min at 4° C. The proteins were separated from the resin by centrifugation and the elution was repeated. Eluted protein was then loaded on to an anion-exchange column (mono Q, Pharmacia) and fractionated with a linear salt gradient [0–500 mM NaCl in 20 mM Tris (pH 7.5)]. The GST-STCH fusion protein eluted between 275 and 325 mM NaCl, while the GST polypeptide eluted at a position corresponding to 175–220 mM NaCl. Pooled fractions were dialyzed against 500 volumes of ATPase buffer [50 mM HEPES (pH 7.0), 25 mM KCl, 2 mM MgSO$_4$] and then concentrated by ultrafiltration (Centricon-10, Amicon Corp.). ATPase assays with the GST-STCH (0.8 μg) were performed as previously described (Flynn, et al., 1989) in the presence or absence of gel purified 1 mM peptide A (sequence: KRQIYTDLEMNRLGK) or 0.5 mM peptide C (sequence: KLIGVLSSLFRPK). Purified STCH (0.8 μg) was incubated in buffer F [20 mM Hepes (pH 7.0), 20 mM NaCl, 2 mM MgCl$_2$, and 1 percent sodium cholate] with 8 μM ATP, 1 μCi of [$^3$H]ATP, and 1 mM peptide A or 0.5 mM peptide C for 10 minutes at 37° C. in a 20-μl reaction. The reaction was terminated by applying 1 μl of sample to polyethyleneimine cellulose thin-layer chromatography plates that had been spotted with carrier nucleotides (0.5 μl each of 10 mM ATP, ADP, and AMP). Chromatography was performed in 0.7M LiCl-1M HCOOH, and the plates were dried. The ATP and ADP spots were located with the aid of an ultraviolet light, excised, and counted. The radioactivity in each spot was expressed as a fraction of the total recovered in each lane. The peptide-independent hydrolysis of ATP (2.6 pmole per 10-minute assay) was subtracted from each curve. For comparison, parallel incubations with bovine BiP (1.0 μg) and the bacterial dnaK (0.9 μg) were also performed. Protein concentrations were determined using the BCA colorimetric analysis using BSA as a standard.

Assay to detect the presence of ATP in a Sample Using STCH

ATPase activity is measured by the method of Shlomai and Koarnberg (*J. Biol. Chem.* 255:6789–6793, 1980, which is hereby incorporated by reference) using TLC on PEI cellulose to separate nucleotides. Reactions typically contain 0.02–1 μg purified STCH or 5 μl of gradient fraction, 10–50μM ATP, 0.1–0.5 μCi [α-$^{32}$P]ATP, 1 mg/ml BSA, 20 mM HEPES, pH 7.2, 20 mM NaCl, 2 mM MgCl$_2$, in a volume of 20 μl reaction are incubated at 37° C. for 1 h. 1 μl of the reaction mixture is then spotted onto a polyethyleneimine (PEI) cellulose plate. Thin layer chromatography is performed against 1:1 ratio of 1M LiCl and 1M HCOOH. The plate is dried, exposed to film and corresponding radioactive spots are excised and counted. ATPase activity is determined from the amount of [$^{32}$P]ADP and [$^{32}$P]AMP generated from [α-$^{32}$P]ATP. Background hydrolysis values obtained from identical incubations lacking purified STCH are subtracted from the data.

EXAMPLE VII

STCH Over Expression Suppresses Oncogene Transformation

Primary rat embryo fibroblasts (REF), grown in DMEM with 10% FCS and 4 mM L-glutamine are transfected with combinations of oncogenes and Stch. Stch is cloned into the eukaryotic expression plasmid pRc/RSV (Invitrogen, San Diego, Calif.). A mutant, transformation-promoting form of p53, p53val135 (see Sturzbecher, H. W., et al. *Oncogene*, 1:201–211, 1987) together with c-myc and c-HA-ras are also incorporated into the eukaryotic expression plasmid pRC/RSV. The sequences for c-myc and ras are available from Battey, et al. and Tabin, et al. respectively (*Cell* 34:779–787, 1983 and *Nature* 300:143–149, 1982). 8×10$^2$ REF cells are seeded in a 90-mm dish and transfected the next day with 5 μg of plasmid DNA containing Stch together with 2.5 μg of each oncogene-containing plasmid by a calcium phosphate transfection procedure (Graham, et al. *Virology* 53:456–467, 1973). Stch-containing plasmid is transfected alone as are each of the oncogene-containing plasmids as controls. 18 hours later the cells are subjected to a glycerol shock (10% glycerol in DMEM plus 10% FCS for 1 min) and washed with DMEM. Foci of cells transformed by the oncogene transfected cells are scored 10–20 days posttransfection and compared to the control transfections. Cells transfected with the transformation-promoting gene in combination with the Stch gene show minimal foci formation as compared with cells transfected with the transformation-promoting gene alone. Foci are isolated and expanded in culture and cells are transfected with either the transformation-promoting gene in combination with the Stch gene or with the Stch gene alone are grown and harvested. 10$^6$ cells from each sample were processed using the Invitrogen FastTrack™ mRNA Isolation Kit (Invitrogen). Equal quantities of the mRNA samples are blotted onto nitrocellulose and processed as Northern Blots. The blots are hybridized with 250 ng $^{32}$P-labelled SEQ ID NO:3 fragments overnight and processed using the hybridization and wash criteria provided in Davis, et al. See Example I. Autoradiograms reveal the increased expression of Stch mRNA in the nontransformed cells transfected with either Stch alone or Stch in combination with a transformation-promoting gene.

EXAMPLE VIII

Use of STCH to promote protein folding during In Vitro Translation, and following Urea Denaturation STCH is useful as an enhancer of protein folding following in vitro translation. IRS-1 is the principle substrate of the insulin receptor and its sequence is disclosed by X.-J. Sun, et al. (*Nature* 352:73, 1991). IRS-1 is tyrosine phosphorylated following insulin stimulation. Knowledge of the interaction between the insulin receptor and IRS-1 is essential to understanding diabetes. IRS has been cloned in eukaryotic cells (Wang, L-M., et al. *Science* 261:1591–1594, 1993); however larger quantities of the protein would be useful for assessing protein activity and for X-ray crystallography. IRS-1 can be isolated in in vitro translation assays by providing an in vitro translation kit, such as those supplied by Stratagene (La Jolla). The kit is supplemented with a physiologic solution containing 1.5M excess of STCH as compared to the expected concentration of protein output. STCH advantageously assists in the protein folding during in vitro translation.

The IRS-1 sequence can also be incorporated into the bacterial expression vector p5E420 (invitrogen, San Diego, Calif.) and the plasmid is transfected into HB101 cells for bacterial expression. The protein is isolated, purified and in the process the protein is denatured. The protein is refolded using 1.0, 1.5, 2.0 and 2.5 molar excess of STCH.

EXAMPLE IX

Use of SEQ ID NO: 15 as a Leader Sequence for Protein Expression in ER

The nucleic acid sequences SEQ ID NO:16 and SEQ ID NO:17 encode the leader sequences for human and rat STCH respectively. The peptide leader sequences encoded by SEQ ID NO:16 and SEQ ID NO:17 are provided in Table II. The human STCH leader peptide is MAREMTILGSAVLTLLLAGYLA and the rat STCH leader peptide is MAGEMTILGSAVLTLLLAGYLA. These sequences are incorporated into a eukaryotic expression vector such as pcDNA1 (Invitrogen, San Diego, Calif.) together with the desired protein to be expressed in the ER.

While particular embodiments of the invention have been described in detail, it will be apparent to those skilled in the art that these embodiments are exemplary rather than limiting, and the true scope of the invention is that defined in the following claims.

What is claimed is:

1. Purified protein comprising SEQ ID NO:2 or SEQ ID NO:14.

2. A purified recombinant or synthetic peptide comprising an amino acid sequence of SEQ ID NO:7 or SEQ ID NO:10.

3. Substantially purified STCH protein characterized by:
   a molecular mobility on a sodium dodecyl sulfate polyacrylamide electrophoresis gel that is equivalent to the molecular mobility of a protein having a molecular weight between 59 and 73 kD;
   a truncated carboxyl terminal peptide-binding domain;
   a protein-independent core ATPase activity; and
   a hydrophobic leader peptide, wherein a gene encoding said STCH protein is expressed in a cell following cell incubation with the calcium ionophore A23187 and wherein the native form of said protein localizes within the microsome lumen of a cell.

* * * * *